(12) United States Patent
Jacob et al.

(10) Patent No.: US 7,238,672 B1
(45) Date of Patent: Jul. 3, 2007

(54) CHIMERIC LYSSAVIRUS NUCLEIC ACIDS AND POLYPEPTIDES

(75) Inventors: Yves Jacob, Maintenon (FR); Pierre Perrin, Montrouge (FR); Noël Tordo, Paris (FR); Chokri Bahloul, Tunis (TN)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 09/958,672

(22) PCT Filed: Apr. 17, 2000

(86) PCT No.: PCT/IB00/00564

§ 371 (c)(1),
(2), (4) Date: Feb. 22, 2002

(87) PCT Pub. No.: WO00/63242

PCT Pub. Date: Oct. 26, 2000

(51) Int. Cl.
*A61K 31/7115* (2006.01)
*C12N 15/00* (2006.01)
*C12N 15/47* (2006.01)
*A61K 39/205* (2006.01)
*A61K 39/295* (2006.01)

(52) U.S. Cl. .................. 514/44; 424/224.1; 424/202.1; 435/91.1; 435/91.33; 435/236; 435/320.1

(58) Field of Classification Search ............. 435/320.1, 435/91.33, 480, 236, 69.1, 69.3, 91.1, 93.32, 435/91.4, 91.41, 91.42, 91.5; 424/9.2, 184.1, 424/192.1, 199.1, 204.1, 224.1, 272.1; 530/300, 530/395; 536/23.1, 23.4, 23.7, 23.72; 514/44
See application file for complete search history.

(56) References Cited

U.S. PATENT DOCUMENTS 4,393,201 A * 7/1983 Curtis et al. ............. 536/23.72
6,673,601 B1   1/2004 Jacob et al.

FOREIGN PATENT DOCUMENTS

| EP | 696 191 B1 | 10/1994 |
|---|---|---|
| WO | WO 90 11092 | 10/1990 |
| WO | WO 93 06223 | 4/1993 |
| WO | WO 95/09249 | 4/1995 |

OTHER PUBLICATIONS

Fields et al. Virology 3rd edition. p. 1142-1143.*
BioDirectoryä' 98 by Amershanpharmaciabiotech pp. 126-127 published 1998.*
Bahloul et al. Vaccine 1998, vol. 15, No. 4, pp. 417-425.*
Xiang et al. Virology. 1995, vol. 209, pp. 569-579.*
Yarosh et al. Vaccine. 1996, vol. 14, No. 13, pp. 1257-1264.*
Taylor et al. Vaccine. 1995, vol. 13, No. 6, pp. 539-549.*
Mebatsion et al. J. Virol. 1995, vol. 69, No. 3, pp. 1444-1451.*
Prehaud et al. Virology. 1989, vol. 173, No. 2, pp. 390-399.*
Xuan et al. Vaccine. May-Jun. 1998, vol. 16, No. 9/10, pp. 969-976.*
Macfarlan, R., I., et al. T Cell resposes to cleaved rabies virus glycoprotein and to synthetic peptides, J. Immunology, vol. 133., pp. 2748-2752 (1984).
Lafon, M., et al., Use of a monoclonal antibody for quantitation of rabies vaccine glycoprotein by enzyme immunoassay, J. Biological Standardization, vol. 13, pp. 295-301 (1985).
Wunner, W.H., et al., Localization of imunogenic domains on the rabies virus glycoprotein, Ann. Inst. Pateur/Virol., vol. 136E, pp. 353-362 (1985).
Perrin, P., et al., Rabies immunosome (subunit vaccine) structure and immunogenicity. Pre- and post-exposure protection studies, Vaccine, vol. 3, pp. 325-332 (1985).
Perrin, P., et al., The influence of the type of immunosorbent on rabies antibody EIA; advantages of purified glycoprotein over whole virus, J. Biological Standardization, vol. 14, pp. 95-102 (1986).
Rogers, S., et al., Amino acid sequences common to rapidly degraded proteins: The PEST hypothesis, Science, vol. 234, pp. 364-369 (1986).
Perrin, P. et al. Interleukin increases protection against experimental rabies, Immunobiology, vol. 177, pp. 199-209 (1988).
Glaudin, Y., et al., Reversible conformational changes and fusion activity of rabies virus glycoprotein, J. Virology, vol. 65, pp. 4853-4859 (1991).
Xiang, Z. Q., et al., Vaccination with a plasmid vector carrying the rabies virus glycoprotein gene induces protective immunity against rabies virus, Virology, vol. 199, pp. 132-140 (1994).
Gaudin, Y. et al., Biological function of the low-pH, fusion-inactive conformation of rabies virus glycoprotein (G):G is transported in a fusion inactive state-like conformation, J. Virology, vol. 69: 5528-5534 (1995).
Editorial, Vaccine, vol. 14, (1996), pp. 579, 691-700.
Perrin, P., et al., The antigen-specific cell-mediated immune response in mice is suppressed by infection with pathogenic lyssaviruses, Research Virology, vol. 147, pp. 289-299 (1996).
Perrin, P., Techniques for the preparation of rabies conjugates, in *Laboratory Techniques in Rabies*, Meslin, F-X, Kaplan, M., and Koprowski, H., eds. pp. 433-445 (1996).

(Continued)

*Primary Examiner*—Bruce R. Campell
*Assistant Examiner*—Bao Qun Li
(74) *Attorney, Agent, or Firm*—Finnegan, Henderson, Farabow, Garrett & Dunner

(57) ABSTRACT

The present invention provides chimeric nucleic acids, preferably contained on an expression vector, that encode chimeric immunogenic polypeptides. The nucleic acids encode at least site III of a *lyssavirus* glycoprotein, which has been found to improve the immunogenicity of *lyssavirus* epitopes for protection from rabies. The chimeric nucleic acids and proteins can also contain antigenic determinants for epitopes other than those of *lyssavirus*. Thus, the invention provides chimeric nucleic acids and polypeptides that elicit a strong immune response to multiple antigens. Use of the methods of the present invention permits DNA vaccination without the need to supply multiple antigens on separate DNA molecules.

4 Claims, 28 Drawing Sheets

OTHER PUBLICATIONS

Figure 1A:
Figure 1A:
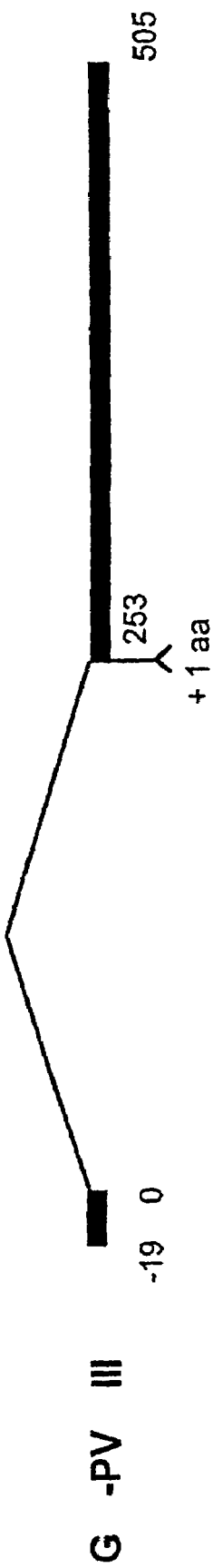
Figure 1A:
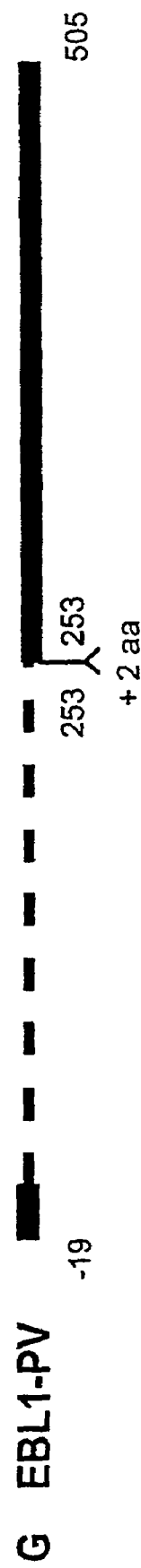
Figure 1C:
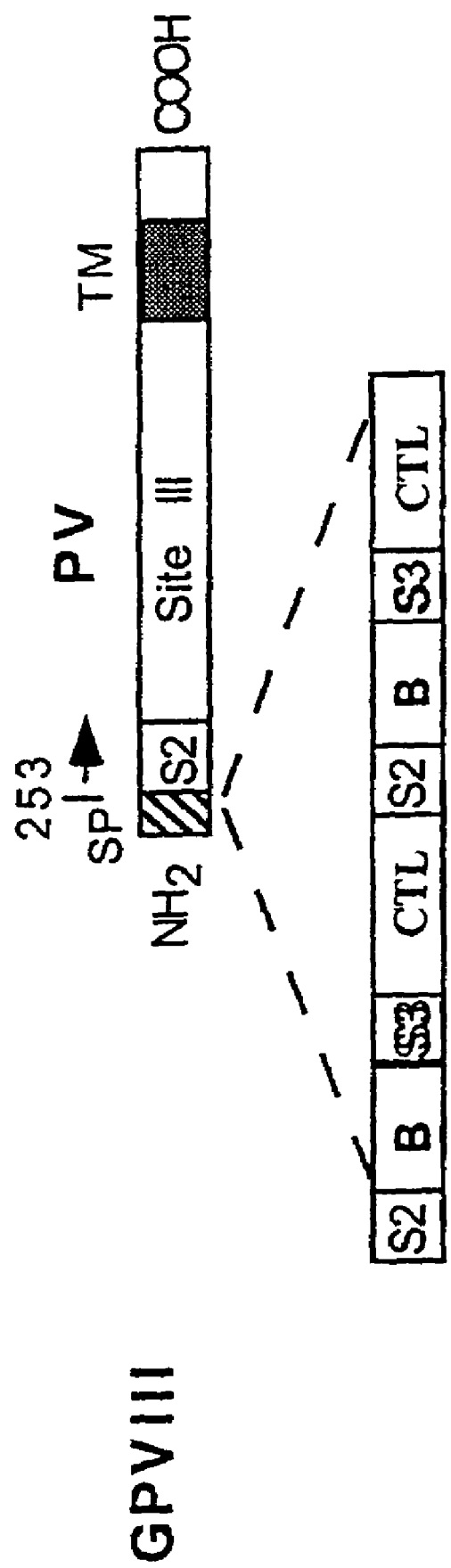

Smith, J.S., et al., A rapid fluorescent focus inhibition test (RFFIT) for determining rabies virus-neutralizing antibody, *in Laboratory Techniques in Rabies*, Meslin, F-X, Kaplan, M., and Koprowski, H., eds. pp. 181-189 (1996).

Amengual, B., et al., Evolution of European bat lyssaviruses, J. General Virology, vol. 78, pp. 2319-2328 (1997).

Donnelly, J.J., et al., DNA Vaccines, Ann. Rev. Immunology, vol. 15, pp. 617-648 (1997).

Gaudin, Y., Folding of rabies virus glycoprotein: epitope acquisition and interaction with endoplasmic reticulum chaperones, J. Virology, vol. 71, pp. 3742-3750 (1997).

Lang, J., et al., Radomised feasibility trial of pre-exposure rabies vaccination with DTP-IPV in infants, Lancet, vol. 349, pp. 1663-1665 (1997).

Pastoret, P.P., et al., Part 2: Vaccination Against Rabies, *in Veterinary Vaccinology*, Pastoret, P-P. et al. eds., pp. 616-628 (1997).

Coulon, P., et al., An avirulent mutant of rabies virus is unable to infect motoneurons in vivo and in vitro, J. Virology, vol. 72, pp. 273-278 (1998).

Tuffereau, C., et al., Neuronal cell surface molecules mediate specific binding to rabies virus glycoprotein expressed by a recombinant baculovirus on the surfaces of Lepidopteran cells, J. Virology, vol. 72, pp. 1085-1091 (1998).

Lodmell, D., L., et al., DNA immunization protects nonhuman primates against rabies virus, Nature Medicine, vol. 4, pp. 949-952 (1998).

Lodmell, D. L., et al., Gene gun particle-mediated vaccination with plasmid DNA confers protective immunity against rabies virus infection, Vaccine, vol. 16, pp. 115-118 (1998).

Thomson, S. A., et al., Delivery of multiple CD8 cytotoxic T cell epitopes by DNA vaccination, J. Immunology, pp. 1717-1723 (1998).

U.S. Appl. No. 10/608,538, filed Jun. 30, 2003, Jacob et al.

Benmansour et al., "Antigenicity of Rabies Virus Glycoprotein", *J. Virol.*, 65(8):4198-4203 (1991).

Buffett et al., "*P. Falciparum Domain* Domain Mediating Adhesion to Chondroitin Sulfate A: A Receptor for Human Placental Infection", *PNAS*, 96(22):12743-48 (1999).

Dietzschold et al., "Structural and Immunological Characterization of a Linear Virus-Neutralizing Epitope of the Rabies Virus Glycoprotein and its Possible Use in a Synthetic Vaccine", *Vaccine*, 64(8):3804-3809 (1990).

Ertl., et al., "Novel Vaccine Approaches", *Journal of Immunology*, 156:3579-3582 (1996).

European Commission COST/STD-3, "Advantages of Combined Vaccines", *Vaccine*, 14(7):693-700 (1996).

Lafay et al., "Immunodominant Epitopes Defined by a Yeast-expressed Library of Random Fragments of the Rabies Virus Glycoprotein Map Outside Major Antigenic Sites", *J.Gen. Virol.*, B77:339-346 (1996).

Liu et al., "Polynucleotide Vaccines: A Potential New Generation of Vaccines," *Proc. Eur. Assoc. Vet. Pharmacol. Toxicol. 6 Meet.*, 301, Abstract Only (1994).

Macy et al., *Vet. Clin. North Am small Anim. Pract.*, Abstract Only, 26(1):103-109 (1996).

Mebatsion et al., "Mokola Virus Glycoprotein and Chimeric Proteins Can Replace Rabies Virus Glycoprotein in the Rescue of Infectious Defective Rabies Virus Particles", *Journal of Virology*, 69(3):1444-1451 (1995).

Paoletti et al., *PNAS*, 93(21):11349-53 (1996).

Tine et al., "NYVAC-Pf7: A Poxvirus-vectored, Multiantigen, Multistage Vaccine Candidate for Plasmodium Falciparum Malaria," *Infection and Immunity.*, 64(9):3833-3844 (1996).

International Search Report in corresponding PCT/IB00/00564.

Jallet et al.; Chimeric lyssavirus glycoproteins with increased immunological potential; J. Virol., (1999) pp. 225-233.

Bahloul et al.; DNA-based immunization for exploring the enlargement of immunological cross-reactivity against the lyssaviruses; Vaccine; (1998) vol. 16, No. 4, pp. 417-425.

Desméziéres et al.; Lyssavirus glucoproteins expressing immunologically potent foreign B cell and cytotoxic T lymphocyte epitopes as prototypes for multivalent vaccines; J. Gen. Virol. (1999), 80:2343-2351.

* cited by examiner

Figure 1A

G Mok-PV  -19  257 | 258  505

Figure 1A (continued)

G  PV-Mok

-19  257 | 258  503

Figure 1A (continued)

```
                                                                                    (SEQ ID NO. 18)
                                                                                    (SEQ ID NO. 19)
                                                                                    (SEQ ID NO. 20)
                                                                                    (SEQ ID NO. 21)
                                                                                    (SEQ ID NO. 22)
                                                                                    (SEQ ID NO. 23)

VI
         230           247         253 258   264              275             290
           *             *           *   *     *                *               *
PV-PV    VLGLRLMDGTWVSMQTSNETKWC...PPGQLINLHDFRSDEIEHLVVEELVKKREECLDALESI
-PVIII   .............................g................................
EBL1-PV  -P-M-----S---L-KTRAPE--SNS......................................
Mok-PV   RP-I--F------FTKPDVHV--...T-N...................................
PV-Mok   ------------------------...I-ND-L------I--DII

Figure 1D:
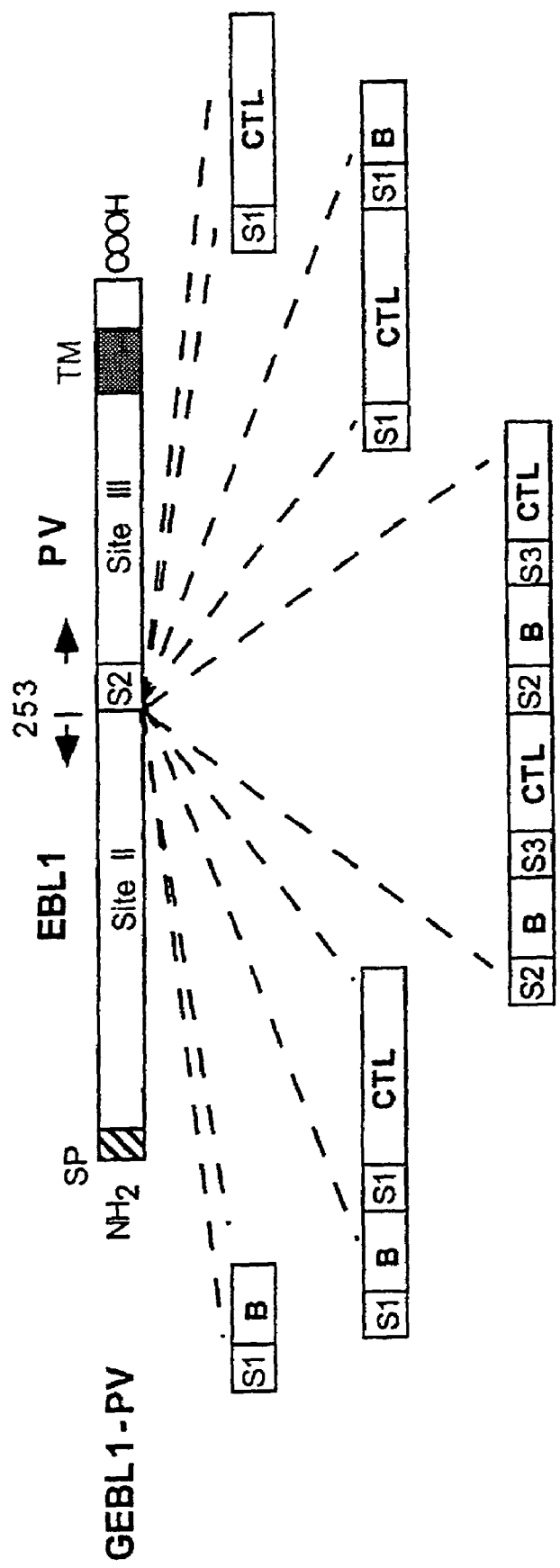
Figure 1E:
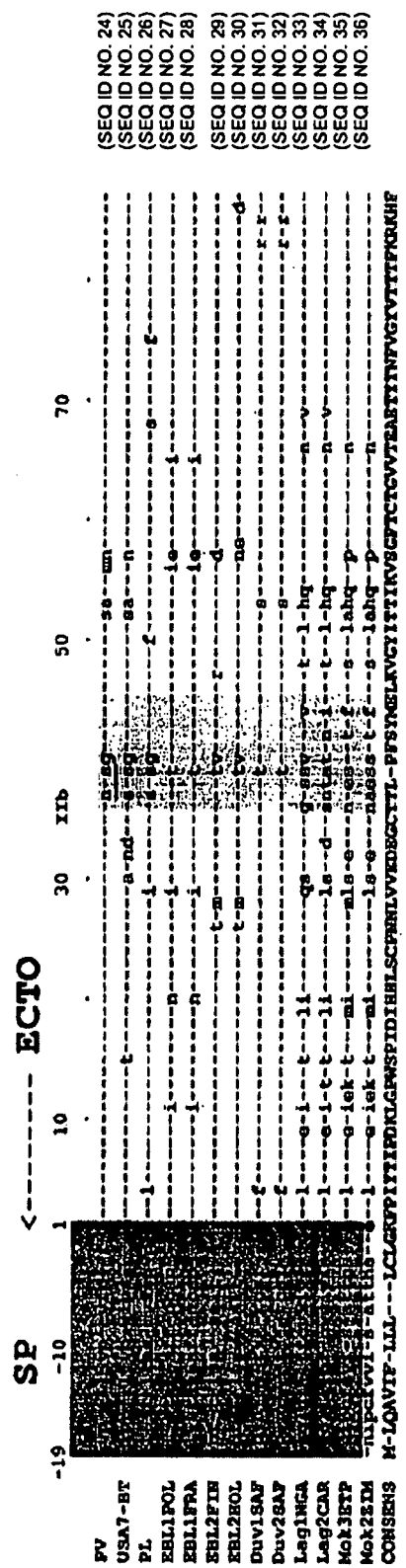

Figure 1E (continued)

FIGURE 1.E continued

```
              430              450              470              490              510
               .                .                .                .                .
PV        --her--v-----n-gk-            --n-septqh--lrgtg-s----p----l-s-------s-gstgl
USA7-BT   --h-r--v-----s-gk-            --nktgstqrghr-srg-m--ap-n--l-s---l--rssstgl
PL        ----qv------s--s--            --c---kkartdrl--d-------------------lxpshfrs
EBL1POL   -t--l-------f-----            ---f----rp---l--------ra-----------v-pp-es
EBL1FRA   -t--l-------f-----            ---f----rp---l--------rav----------v--tsss
EBL2FIN   ----q-------------            --ar---rp--------------rp----------va-g--qs
EBL2HOL   ----q-------------            ---hkkra---v-----------rp----------va-g--qs
Duv1SAF   -tnqk-------------            --kkra-----v--------------------------ve-g--qs
Duv2SAF   -tnqk-------------            --f-n--ks--s-v---t-----i-kgngpv------s--t-dvrnttpstrs
Lag1NGA   --h-lv-dv-----d-sl            --frk-kks--g-v---t-----i-kgngpv------s--t-dvrnttpstrs
Lag2CAR   -i--l--dv-----s-gl            --krg--nsptnr-dlp-glsttpqks----s------gtsnv
Mok3ETP   ----sv-dv-----h-gfw           --kkt--t-tsmsr-dpp-slsttpqsrs--vs------gssnv
Mok2ZIM   --h-sv-dv-----h-gfw           --mr----slratqdiplsvspapvpra--vs----s-glpgt
CONSENS   DVQK-ISGIDLGLPEWKRYFLIGASALALALIIAVCCKRVKRRR--KPNP-ELIRKVSVTSQSGKVIPSWESYK-GT-G

ECTO----->     TM         <-----  ENDO
```

FIGURE

CHIMERIC LYSSAVIRUS NUCLEIC ACIDS AND POLYPEPTIDES

The present invention relates to chimeric *lyssavirus* nucleic acids, and chimeric polypeptides and proteins encoded by these nucleic acids. More particularly, the invention relates to chimeric *lyssavirus* nucleic acids and proteins that can be used in immunogenic compositions, such as vaccines. Thus, the invention also relates to carrier molecules for expressing chimeric *lyssavirus* nucleic acids, methods of producing chimeric *lyssavirus* proteins and polypeptides, and methods of treating individuals to ameliorate, cure, or protect against *lyssavirus* infection.

Rabies is an encephalopathic disease caused by members of the *Lyssavirus* genus within the Rhabdoviridae family. Rabies infects all warm-blooded animals and is almost invariably fatal in humans if not treated. On the basis of nucleotide sequence comparisons and phylogenetic analyses, the *Lyssavirus* genus has been divided into 7 genotypes (GT). GT1 includes the classical rabies viruses and vaccine strains, whereas GT2 to GT7 correspond to rabies-related viruses including Lagos bat virus (GT2); Mokola virus (GT3); Duvenhage virus (GT4); European bat *lyssavirus* 1 (EBL-1: GT5); European bat *lyssavirus* 2 (EBL-2: GT6); and Australian bat *lyssavirus* (GT7).

Based on antigenicity, the *Lyssavirus* genus was first divided into four serotypes. More recently, this genus was divided into two principal groups according to the cross-reactivity of virus neutralizing antibody (VNAb): Group 1 consists of GT1, GT4, GT5, GT6, and GT7, while Group 2 consists of GT2 and GT3. Viruses of group 2 are not pathogenic when injected peripherally in mice. Virulence of *lyssaviruses* is dependent, at least in part, on the glycoprotein present in the viral coat. Interestingly, the glycoproteins of group 2 viruses show a high degree of identity, in the region containing amino acids that play a key role in pathogenicity, to the corresponding sequence of avirulent GT1 viruses (see, for example, Coulon et al., 1998, "An avirulent mutant of rabies virus is unable to infect motoneurons in vivo and in vitro", *J. Virol.* 72:273–278).

Rabies virus glycoprotein (G) is composed of a cytoplasmic domain, a transmembrane domain, and an ectodomain. The glycoprotein is a trimer, with the ectodomains exposed at the virus surface. The ectodomain is involved in the induction of both VNAb production and protection after vaccination, both pre- and post-exposure to the virus. Therefore, much attention has been focused on G in the development of rabies subunit vaccines. Structurally, G contains three regions, the amino-terminal (N-terminal) region, a "hinge" or "linker" region, and the carboxy-terminal (C-terminal) region. (See FIG. 1.)

As depicted in FIG. 1, it is generally thought that the glycoprotein (G) ectodomain has two major antigenic sites, site II and site III, which are recognized by about 72.5% (site II) and 24% (site III) of neutralizing monoclonal antibodies (MAb), respectively. The site II is located in the N-terminal half of the protein and the site III is located in the C-terminal half of the protein. The two halves are separated by a flexible hinge around the linear region (amino acid 253 to 257).

The G ectodomain further contains one minor site (site a), and several epitopes recognized by single MAbs (I: amino acid residue 231; V: residue 294, and VI: residue 264) (5, 10, 18, 21 ref 2). Site II is conformational and discontinuous (amino acid residues 34 to 42 and amino acid residues 198 to 200, which are associated by disulfide bridges), whereas site III is conformational and continuous (residues 330 to 338). Lysine 330 and arginine 333 in site III play a key role in neurovirulence and may be involved in the recognition of neuronal receptors (see, for example, Coulon et al., supra, and Tuffereau et al., 1998, "Neuronal cell surface molecules mediate specific binding to rabies virus glycoprotein expressed by a recombinant baculovirus on the surfaces of lepidopteran cells", *J. Virol.* 72:1085–1091). Sites II and III seem to be close to one another in the three dimensional structure and exposed at the surface of the protein (Gaudin, Y., 1997, "Folding of rabies virus glycoprotein: epitope acquisition and interaction with endoplasmic reticulum chaperones", *J. Virol.* 71:3742–3750). However, at low pH, the G molecule takes on a fusion-inactive conformation in which site II is not accessible to MAbs, whereas sites a and III remain more or less exposed (Gaudin, Y. et al., 1995, "Biological function of the low-pH, fusion-inactive conformation of rabies virus glycoprotein (G): G is transported in a fusion-inactive state-like conformation", *J. Virol.* 69:5528–5533; Gaudin, Y., et al., 1991, "Reversible conformational changes and fusion activity of rabies virus glycoprotein", *J. Virol.* 65:4853–4859).

Moreover, several regions distributed along the ectodomain are involved in the induction of T helper (Th) cells (MacFarlan, R. et al., 1984, "T cell responses to cleaved rabies virus glycoprotein and to synthetic peptides", *J. Immunol.* 133:2748–2752; Wunner, W. et al, 1985, "Localization of immunogenic domains on the rabies virus glycoprotein", *Ann. Inst. Pasteur,* 136 E:353–362). Based on these structural and immunological properties, it has been suggested that the G molecule may contain two immunologically active parts, each potentially able to induce both VNAb and Th cells (Bahloul, C. et al, 1998, "DNA-based immunization for exploring the enlargement of immunological cross-reactivity against the *lyssaviruses*", *Vaccine* 16:417–425).

Currently available vaccines predominantly consist of, or are derived from, GT1 viruses, against which they give protection. Many vaccine strains are not effective against GT4, and none are effective against GT2 or GT3. However, the protection elicited against GT4 to 6 depends on the vaccine strain. For example, protection from the European bat *lyssaviruses* (GT5 and GT6), the isolation of which has become more frequent in recent years, by rabies vaccine strain PM (Pitman-Moore) is not robust. Strain PM induces a weaker protection against EBL1 (GT5) than the protection it provides against strain PV (Pasteur virus).

Because, in part, of the importance of rabies in world health, there is a continuing need to provide safe, effective, fast-acting vaccines and immunogenic compositions to treat and prevent this disease. Many approaches other than use of whole-virus preparations have been proposed and/or pursued to provide an effective, cost-efficient immunogenic composition specific for rabies viruses. For example, as discussed above, subunit vaccines have been developed. Also, vaccines that could generate an immune response to multiple rabies serotypes as well as various other pathogens has been proposed as having some value (European Commission COST/STD-3, 1996, "Advantages of combined vaccines", *Vaccine* 14:693–700). In fact, use of a combined vaccine of diphtheria, tetanus, whole cell pertussis, inactivated poliomyelitis, and rabies has recently been reported (Lang, J. et al., 1997, "Randomised Feasibility trial of pre-exposure rabies vaccination with DTP-IPV in infants", *The Lancet* 349:1663–1665). Combined vaccines including rabies have also been used for immunization of dogs (distemper, hepatitis, leptospirosis, and parvo-canine viruses), cats (panleukopenia, calici- and parvo-feline viruses), and cattle (foot and mouth disease virus) (Pastoret, P-P. et al., 1997, "Vaccination against rabies", In *Veterinary Vaccinology*, Pastoret, P-P. et al., Eds. (Elsevier): 616–628 23).

Moreover, vaccines produced in tissue culture are expensive to produce despite some attempts to reduce their cost. Consequently DNA vaccines, which are less expensive to produce and offer many advantages, would constitute a valuable alternative. Reports of DNA vaccinations include mouse inoculation with plasmids containing the gene encoding the rabies virus glycoprotein (G). Such inoculation is very potent in inducing humoral and cellular immune responses in association with protection against an intracerebral challenge (see, for example, Lodmell, D. et al., 1998, "DNA immunization protects nonhuman primates against rabies virus", *Science Med.* 4:949–952; Xiang, Z. et al., 1994, "Vaccination with a plasmid vector carrying the rabies virus glycoprotein gene induces protective immunity against rabies virus", *Virol.* 199:132–140; and Lodmell, D. et al., 1998, "Gene gun particle-mediated vaccination with plasmid DNA confers protective immunity against rabies virus infection", *Vaccine* 16, 115). DNA immunization can also protect nonhuman primates against rabies (Lodmell et al, 1998, supra).

Because administration of plasmid DNA generates humoral and cellular immune responses, including cytotoxic T-Lymphocyte (CTL) production (for review see Donnelly, J. et al., 1997, "DNA Vaccines", *Annu. Rev. Immunol.* 15:617–648) and is based on a versatile technology, immunization with plasmid DNA may offer a satisfying prospect for multivalent vaccines. However, the use of a mixture of plasmids or a single plasmid expressing several antigens is believed to induce interference problems at both transcriptional and immunological levels (Thomson, S. et al., 1998, "Delivery of multiple CD8 cytotoxic cell epitopes by DNA vaccination", *J. Immunol.* 160: 1717–1723). Therefore, there exists a need to develop and produce multivalent DNA-based vaccines that are effective against rabies and various other diseases; that are safe; and that are cost-efficient to produce and use.

The present invention provides chimeric nucleic acid sequences that encode chimeric polypeptides that induce immunogenic responses in individuals. The nucleic acids of the invention can be expressed to provide chimeric polypeptides that elicit an immune response against rabies and/or rabies-related viruses as well as other pathogenic or otherwise undesirable organisms or polypeptides. Further, the nucleic acids of the invention themselves can elicit at least a portion of the immune response. Thus, the chimeric nucleic acids of the invention can be used to make an immunogenic composition, which can be used to treat an individual.

The present invention also provides a carrier molecule, such as a DNA expression vector, comprising the nucleic acid of the invention, which encodes a chimeric polypeptide. The carrier molecule of the invention can be used as an immunogenic composition, or as part of an immunogenic composition, to elicit the desired immune response. The desired immune response can be a protective response to rabies or rabies-related viruses as well as other organisms or polypeptides. Thus, the carrier molecules of the invention can be used to make an immunogenic composition, which can be used to treat an individual. The carrier molecule can also be used to produce a chimeric polypeptide.

The present invention thus provides a chimeric (fusion) protein that is encoded by the nucleic acid of the invention, or by a nucleic acid sequence present in the carrier molecule of the invention. The chimeric protein can be used to elicit an immunogenic response in an individual. The fusion protein comprises the site III antigenic determinant of a *lyssavirus* glycoprotein, and can comprise other antigenic sites from one or multiple other polypeptides. Thus, the chimeric polypeptide of the invention can be used to make an immunogenic composition, which can be used to treat an individual.

The present invention further provides immunogenic compositions, including vaccines, that elicit an immunological response in individuals to whom they are administered. The present invention includes immunogenic compositions comprising a polynucleotide sequence that encodes a chimeric (or fusion) polypeptide, or the chimeric polypeptide so encoded, which elicits the immune response. The immunogenic compositions and vaccines of the present invention provide an increased level of immune stimulation and enhanced protection against rabies viruses, and broaden the spectrum of protection against rabies-related viruses, than is provided by immunogenic compositions known in the art. The immunogenic compositions also provide multiple immunogenic active sites for induction of an immune response against non-rabies and not rabies-related epitopes.

In view of the above embodiments of the invention, it is evident that the present invention also provides a method of producing a chimeric nucleic acid, a method of producing a carrier molecule, a method of producing a fusion protein, and a method of making an immunogenic composition, such as a vaccine. The immunogenic composition so made can be used to treat (e.g., immunize) individuals.

Included in the invention is the use of the nucleic acid, polypeptide, and/or carrier molecule of the invention to elicit an immune response, such as a protective immune response. Thus, the invention includes the use of a vaccine comprising the polynucleotide, polypeptide, and/or carrier molecule of the invention to treat, either prophylactically or therapeutically, an individual. Therefore, the invention includes prophylactic treatment methods, therapeutic treatment methods, and curative treatment methods.

The inventors have created chimeric nucleic acid sequences that encode chimeric polypeptides that induce immunogenic responses in individuals. As discussed above, it is known in the art that DNA can elicit both humoral and cellular immune responses. In doing so, it is possible that the nucleic acids themselves can induce at least part of the immunogenic response. Thus, according to the invention, the chimeric nucleic acids and carrier molecules can provide or promote an immunogenic response when used according to the invention.

As used herein, "chimeric" and "fusion" are used interchangeably and in reference to both nucleic acids and polypeptides. These terms refer to nucleic acids and polypeptides that comprise sequences that are not found naturally associated with each other in the order or context in which they are placed according to the invention. For example, a chimeric glycoprotein can comprise a C-terminal region from a rabies GT1 and an N-terminal region from a rabies GT3 or GT5. Further, a chimeric nucleic acid can comprise a short segment from one portion of a rabies genotype linked directly to another segment from the same genotype, where the two segments are not naturally adjacent each other. Thus, a chimeric or fusion nucleic acid or polypeptide does not comprise the natural sequence of a rabies virus in its entirety, and may comprise heterologous (from another strain of *lyssavirus*, or from another organism altogether) sequences. Fusion/chimeric proteins have the two (or more) heterologous segments joined together through normal peptide bonds, while fusion/chimeric nucleic acids have the two (or more) heterologous segments joined together through normal phosphodiester bonds.

In one aspect of the invention, the chimeric nucleic acids comprise a) a sequence encoding site III of a glycoprotein, b) a sequence encoding the transmembrane domain (or a portion thereof that is functionally equivalent to the transmembrane domain) of a glycoprotein, and c) a sequence that encodes the cytoplasmic domain of the glycoprotein of a *lyssavirus*. In preferred embodiments of this aspect of the invention, the chimeric nucleic acids further comprise a sequence encoding site II of a *lyssavirus* glycoprotein. In embodiments, the sequence encoding the transmembrane domain (or portion thereof) is a sequence from a transmembrane glycoprotein of a *lyssavirus*. In other embodiments, the sequence is from a transmembrane glycoprotein other than a glycoprotein from a *lyssavirus*. For example, it can be from a glycoprotein from another organism, or from a transmembrane protein that is not a glycoprotein. In embodiments, the sequence encoding the transmembrane domain (or portion thereof) and the sequence encoding the cytoplasmic domain are from the same *lyssavirus*. In embodiments of this aspect of the invention, the sequence encoding site III and the cytoplasmic domain are from the same protein, preferably a *lyssavirus* protein, such as a *lyssavirus* glycoprotein.

In a preferred embodiment of this aspect of the invention, the chimeric nucleic acid includes sequences that encode a site III sequence of a *lyssavirus* glycoprotein, a site II sequence of a *lyssavirus* glycoprotein, a transmembrane domain of a transmembrane protein, and a cytoplasmic domain of a *lyssavirus* glycoprotein. The transmembrane domain can be from a *lyssavirus* or another organism. It is highly preferred that the chimeric nucleic acid of the invention comprise sequences encoding an antigenic protein (or antigenic portion thereof), especially between the sequences encoding sites II and III.

The sequences encoding site II and site III are sequences encompassing site II and site III of a glycoprotein of a *lyssavirus*, respectively. In embodiments, the sequence encoding site III is not identical to any of the known site III sequences of *lyssaviruses*, but shows at least 60% identity with one of the *lyssavirus* sequences, extending 30 bp on each side of the site III sequence. Sequence analysis and phylogenetic studies are performed using various packages: GCG (version 8.1, 1994), CLUSTAL W (Thompson, 1994 #1040), PHYLIP (Version 3.5: Felseustein, 1993, #1042), and GDE (Genetic Data Environment, Version 2.2: Institute Pasteur Scientific Computer Service—S.I.S.).

In preferred embodiments of this aspect of the invention, the site III sequence is from rabies virus strain PV, or shows at least 60% identity to that site III sequence. Highly satisfactory results are obtained with the following constructs, displayed in FIG. 1: PV—PV or PV III or EBL1-PV or MOK-PV. The basis module has to contain at least a PV III sequence.

The inventors have found that the presence of site III of the *lyssavirus* glycoproteins improves the immunogenicity of compositions comprising the glycoprotein, or portions thereof. Thus, the present invention includes chimeric nucleic acids that comprise a sequence encoding site III of a *lyssavirus* glycoprotein that is functionally, operatively, and physically linked to a homologous or heterologous sequence encoding a transmembrane domain from natural or synthetic sequence encoding a transmembrane protein (or a portion thereof that is functionally equivalent to the transmembrane domain), and a sequence encoding a cytoplasmic domain (or a portion thereof that is sufficient to stably exist cytoplasmically) from a glycoprotein. Preferably, the glycoprotein is that of a virus and particularly that of a *lyssavirus*. The chimeric nucleic acid sequences can all be from the same *lyssavirus*, can be selected from various *lyssaviruses*, or can be from both *lyssaviruses* and other viruses and organisms. In preferred embodiments, the nucleic acid sequences encoding the site III and the cytoplasmic domain are from the same *lyssavirus*.

In addition, the chimeric nucleic acid of the invention can comprise a sequence that encodes an antigenic polypeptide, or an antigenic portion thereof, from another virus or organism (a heterologous sequence). For example, the chimeric nucleic acid can comprise, in addition to the elements set forth above, a sequence that encodes an epitope from *leishmania*, diphtheria, tetanus, poliomyelitis, foot and mouth disease virus, herpes viruses, canine distemper viruses, parvovirus, and feline immunodeficiency virus. Alternatively, or in addition, the chimeric nucleic acid can comprise a sequence that encodes a tumor antigen. The sequence encoding the heterologous polypeptide (or antigenic portion thereof) is fused (in frame) with the coding sequence detailed above, at any site that results in a functional product. In this way, the chimeric nucleic acid of the invention provides the coding sequence for multiple antigenic determinants, including, but not limited to, rabies virus epitopes.

The chimeric nucleic acids of the invention can be used to make an immunogenic composition. The immunogenic composition can consist essentially of the chimeric nucleic acid or can comprise the chimeric nucleic acid in addition to other components, including, but not limited to, adjuvants, excipients, stabilizers, supra molecular vectors as described in European Patent No. 696,191 (Samain et al.), and antigens. The components typically included in immunogenic compositions are well known to the skilled artisan in the field, as are the techniques for preparation of immunogenic compositions, such as vaccines. Therefore, preparation of the immunogenic composition can be achieved by the skilled artisan using well known techniques without undue or excessive experimentation.

In another aspect of the invention, the chimeric nucleic acid of the invention is present as part of a carrier molecule. The core of the carrier molecule can be any molecule that is known to be useful to maintain, and preferably express, a heterologous polypeptide-encoding nucleic acid. The core of the carrier molecule can be, for example, a plasmid, a phage, a phagemid, a cosmid, a virus, or a yeast artificial chromosome (YAC). Such core carrier molecules are also commonly referred to as vectors or expression vectors, and are well-known to the skilled artisan and are widely available to the public. The carrier molecule of the invention can be provided as a naked nucleic acid, or packaged, such as in a viral shell or coat. The carrier molecule can be provided as DNA or RNA. Modified forms of these two nucleic acids are included within the scope of the invention. Preferably, the carrier molecule comprises sequences that permit transcription of the chimeric nucleic acids of the invention. These sequences are operably linked to the chimeric nucleic acids of the invention (i.e. their operation/function directly affects expression of the chimeric nucleic acid). In embodiments, these sequences include regulatory elements that allow controlled expression of the chimeric nucleic acids so that expression of the chimeric nucleic acids can be regulated, by, for example, delaying expression until desired or expressing the chimeric nucleic acids in certain tissues or cell types only. Such control elements are well-known to the artisan in the field and can routinely be inserted or removed from the carrier molecules as desired or necessary using well-known molecular biology techniques and reagents.

In one embodiment of the invention, a carrier molecule according to the invention comprises nucleic acids encoding a) the site III of the glycoprotein of a *lyssavirus*, b) a transmembrane domain of a glycoprotein (or a portion thereof that is functionally equivalent to the transmembrane domain), and (c) a sequence that encodes the cytoplasmic domain of the glycoprotein of a *lyssavirus*. In preferred embodiments of this aspect of the invention, the carrier molecule further comprises a sequence encoding site II of a *lyssavirus* glycoprotein. In embodiments, the sequence encoding the transmembrane domain (or portion thereof) is a sequence from the glycoprotein of a *lyssavirus*. In other embodiments, the sequence is from a transmembrane glycoprotein other than a glycoprotein from a *lyssavirus*. In embodiments, the sequence encoding the transmembrane domain (or portion thereof) and the sequence encoding the cytoplasmic domain are from the same *lyssavirus*. In embodiments, the sequence encoding the site III and the cytoplasmic domain are from the same *lyssavirus*.

In a preferred embodiment, the carrier molecule further comprises at least one antigenic sequence other than site III or site II of a *lyssavirus*. The additional antigenic sequence(s) can be from any organism and includes, but is not limited to, antigenic sequences from parasites (for example *leishmania*), bacteria, viruses, and tumor cells. The carrier molecule of the present invention, by providing the region of *lyssavirus* glycoprotein required for enhanced immunogenicity (site III), allows the production of a high level immune response to not only the *lyssavirus* antigens (sites III and II), but to the heterologous antigen(s) fused to the *lyssavirus* sequences. The carrier molecule can thus be used to elicit an immune response to multiple antigens from different organisms.

The carrier molecule of the invention preferably comprises a chimeric sequence that encodes a chimeric polypeptide that comprises at least one antigenic determinant, which is site III of a *lyssavirus*. More preferably, the carrier molecule comprises a chimeric sequence that encodes a chimeric polypeptide that comprises the site III of a *lyssavirus* and at least one other antigenic determinant selected from the group consisting of an antigen from the same *lyssavirus* from which the site III was derived and a heterologous antigen. The other antigenic determinants include, but are not limited to, those of pathogenic parasites, viruses, and bacteria, and those of tumor cells. The carrier molecules of the invention can be used to make an immunogenic composition. The immunogenic composition can consist essentially of the carrier molecule or can comprise the carrier molecule in addition to other components, including, but not limited to, adjuvants, excipients, stabilizers, supra molecular vectors (EP 696,191, Samain et al.), and antigens. The components typically included in immunogenic compositions are well known to the skilled artisan in the field, as are the techniques for preparation of immunogenic compositions, including vaccines. Preparation of the immunogenic composition is a routine matter that can be achieved by the skilled artisan using well known techniques without undue or excessive experimentation and thus need not be described in detail herein.

In another aspect, the present invention provides a chimeric polypeptide or protein that is encoded and/or expressed by the chimeric nucleic acid and/or carrier molecule of the present invention. The chimeric polypeptide comprises a) site III of a *lyssavirus* glycoprotein, b) a transmembrane domain of a glycoprotein (or a functional portion thereof), and c) a cytoplasmic domain of the glycoprotein of a *lyssavirus*. In preferred embodiments of this aspect of the invention, the chimeric polypeptides further comprise site II of a *lyssavirus* glycoprotein. In embodiments, the transmembrane domain (or portion thereof) is from the glycoprotein of a *lyssavirus*. In other embodiments, the transmembrane domain (or portion thereof) is from a transmembrane glycoprotein other than a glycoprotein from a *lyssavirus*. In other embodiments, the transmembrane domain (or portion thereof) and the cytoplasmic domain are from the same *lyssavirus*. In embodiments, the site III and the cytoplasmic domain are from the same *lyssavirus*.

Site II and site III can be obtained from any *lyssavirus*, and both can, but do not necessarily, come from the same *lyssavirus*. Further, the sequence of site II and/or site III does not have to be identical to a site II or site III of a glycoprotein of a *lyssavirus*. In embodiments, the sequence of one or both is not identical to any of the known site II or site III sequences of *lyssaviruses*, but shows at least 60% identity with one of the *lyssavirus* sequences, extending 10 residues on each side of the site II or site III sequence.

In preferred embodiments, the chimeric polypeptide of the invention further comprises at least one antigenic determinant other than *lyssavirus* glycoprotein site III or site II. The other antigenic determinant can be an antigenic protein, or antigenic portion thereof, from another rabies virus or rabies related virus, from another virus, from a parasite, a bacterium, or any other organism or cell that expresses an undesirable antigenic determinant. Thus, the invention provides a chimeric polypeptide comprising, as the only antigenic determinant, site III of a *lyssavirus*. Because antigenicity is dependent, at least to some extent, on the individual to whom the immunogenic composition is administered, a chimeric polypeptide having only one antigenic determinant in one organism may have more than one antigenic determinant in another. However, according to the invention, if a chimeric polypeptide has only one antigenic determinant in at least one individual, regardless of the number it has in other individuals, it is a chimeric polypeptide according to this embodiment of the invention.

The invention also provides a chimeric polypeptide with multiple antigens including, but not limited to, rabies antigens. The chimeric polypeptide can be used as, or as part of, an immunogenic composition, such as a vaccine. Thus, the polypeptide of the invention is an immunogenic polypeptide that contains at least one region (which can be isolated as a fragment) that induces an immunogenic response. In embodiments where a site II, a site III, and another antigenic determinant are present, it is preferably, but not necessary, for the other antigenic determinant to be located between site II and site III in the linear (primary) amino acid sequence of the polypeptide. A preferred antigen other than site II or site III is a tumor antigen from a tumor cell.

Preferably, the chimeric nucleic acids, carrier molecules, and chimeric polypeptides (the "molecules") of the invention are isolated and/or purified. The terms "isolated" and "purified" refer to a level of purity that is achievable using current technology. The molecules of the invention do not need to be absolutely pure (i.e., contain absolutely no molecules of other cellular macromolecules), but should be sufficiently pure so that one of ordinary skill in the art would recognize that they are no longer present in the environment in which they were originally found (i.e., the cellular milieu). Thus, a purified or isolated molecule according to the invention is one that has been removed from at least one other macromolecule present in the natural environment in which it was found. More preferably, the molecules of the invention are essentially purified and/or isolated, which means that the composition in which they are present is almost completely, or even absolutely, free of other macromolecules found in the environment in which the molecules of the invention are originally found. Isolation and purification thus does not occur by addition or removal of salts, solvents, or elements of the periodic table, but must include the removal of at least some macromolecules.

As can be seen from the above disclosure, the invention provides an immunogenic composition. The immunogenic composition can comprise the chimeric nucleic acid, chimeric protein, and/or carrier molecule of the invention. For example, the chimeric polypeptides of the invention can be used to make an immunogenic composition. The immunogenic composition can consist essentially of the chimeric polypeptide or can comprise the chimeric polypeptide in addition to other components, including, but not limited to, adjuvants, excipients, stabilizers, supra molecular vectors (EP 696,191, Samain et al.) and antigens. The components typically included in immunogenic compositions are well known to the skilled artisan in the field, as are the techniques for preparation of immunogenic compositions, such as vaccines. Therefore, preparation of the immunogenic composition can be achieved by the skilled artisan using well known techniques without undue or excessive experimentation.

The immunogenic composition according to the invention is a composition that elicits an immune response at least to *lyssaviruses*. Because the chimeric nucleic acids (and thus carrier molecules and polypeptides) of the invention can comprise antigenic determinants from the various *lyssavirus* genotypes in various combinations, the immunogenic composition of the invention can provide a broad spectrum of protection against *lyssaviruses* that induce encephalomyelitis, including rabies viruses. Furthermore, because sequences encoding multiple *lyssavirus* epitopes can be included in one chimeric nucleic acid, the immunogenic composition of the invention can provide an immune response to multiple (including all) genotypes of *lyssavirus*. Preferably, the immunogenic composition of the invention elicits both a cellular and a humoral immune response.

In addition, the immunogenic composition of the invention can provide epitopes from not only *lyssaviruses*, but from any other organism as well (including antigens produced by human cells, such as undesirable antigens found on the surface of cancerous cells). This permits the construction of immunogenic compositions, including, but not limited to vaccines, having broad applicability in that a single composition can be used to elicit an immune response to multiple pathogens. For example, an immunogenic composition can be made that provides a protective immunological response to a broad range of *lyssaviruses* while at the same time providing a protective response to other viruses such as polio and influenza. Such a multivalent immunogenic composition is provided by the chimeric nature of the nucleic acids and polypeptides of the invention, as well as the presence of site III of a *lyssavirus*, which confers a strong immunogenic response to the epitopes of the antigenic polypeptide.

The immunogenic composition of the invention elicits an immunogenic response in individuals to whom it is administered. The immunogenic response can elicit a protective immune response, but such a response is not necessary. According to the invention, immunogenic compositions that elicit a protective response are referred to as vaccines. The immunogenic responses can be enhanced or otherwise modified by the inclusion of components, in addition to the chimeric nucleic acids, chimeric proteins, and carrier molecules of the invention. Alternatively, the immunogenic compositions can consist essentially of the chimeric nucleic acids, chimeric proteins, and carrier molecules of the invention. Thus, the invention encompasses DNA vaccines comprising the chimeric nucleic acids and/or the carrier molecules of the invention.

The invention thus provides a method of making an immunogenic composition. In one embodiment, the method comprises isolating and/or purifying the chimeric nucleic acid or polypeptide or the carrier molecule. In another embodiment, the method comprises isolating the nucleic acid or polypeptide or the carrier molecule, then combining it with additional components. The additional components can be any suitable compound that does not have an adverse effect on the immunogenicity, safety, or effectiveness of the nucleic acid, polypeptide, or carrier molecule of the invention. The additional components include, but are not limited to, compounds and additives that are typically added to immunogenic compositions to enhance immunogenicity, stability, and bioavailability. Such additives are disclosed above and are well known to the skilled artisan.

In another embodiment of this aspect of the invention, the method of making an immunogenic composition is a method of expressing a chimeric (hybrid) polypeptide for use in the production of an immunogenic composition. In this embodiment, the chimeric nucleic acid or carrier molecule of the invention is expressed (transcribed and translated) so that the chimeric polypeptide is produced. The chimeric polypeptide so produced is then isolated and/or purified to an acceptable level so that it can be used to make an immunogenic composition. Production of an immunogenic composition in this embodiment of the invention is according to the disclosure herein. As used herein, a polypeptide is a polymer of amino acids and includes peptides (more than 3 amino acids in length), and proteins (more than 100 amino acids in length). Production of the chimeric polypeptide can be performed in vivo or in vitro. Preferably, production occurs in vivo by expression in bacterial or tissue cultures, and the chimeric polypeptide is isolated from those cultures using known protein purification techniques.

In a further aspect of the invention, methods of making the chimeric nucleic acid, carrier molecules, and chimeric polypeptides of the invention are provided. The methods include commonly known genetic engineering techniques that are well-known to the skilled artisan. Any known technique that is routinely practiced by the skilled artisan can be used to produce and purify the chimeric molecules of the invention. The novelty of the invention does not lie in these techniques, but in the chimeric molecules constructed through the use of them. In this aspect, the methods can be used to make a nucleic acid or carrier molecule for use in the production of an immunogenic composition, such as a DNA vaccine. The invention thus includes a method of making a composition for use in a DNA vaccine.

The invention also provides methods of treating individuals with the immunogenic compositions of the invention. Preferably, the method is a method of vaccination. The method comprises administering the immunogenic compositions to individuals, or patients, in need of treatment, suspected of needing treatment, or desiring prophylactic (protective) treatment for a disease or disorder. Any known method of administration can be used in this aspect of the invention, including, but not limited to, injection with syringe and needle (e.g., subcutaneous, intramuscular, intravenous), oral or mucosal administration, inhalation, topical administration (e.g., applying directly to the skin), and by suppository.

In an embodiment of this aspect of the invention, the method comprises administering the chimeric nucleic acids of the invention to an individual in an amount sufficient to elicit an immunogenic reaction in the recipient. Preferably, this response is a protective response. The amount of nucleic acid necessary for such an immunization can be determined by those of skill in the art without undue or excessive experimentation. For example, compositions comprising the chimeric nucleic acids and carrier molecules of the invention can be administered in an amount of 40 to 100 µg intramuscularly in one or several injections. A 100 µg dosage is generally useful for dogs, and a 40 µg dosage for mice (weight 20 g).

In another embodiment of this aspect of the invention, the method comprises administering the chimeric polypeptides of the invention to an individual. Preferably, the response is a protective response. The amount of polypeptide necessary for such an immunization can be determined by those of skill in the art without undue or excessive experimentation. For example, compositions comprising the chimeric polypeptides of the invention can be administered in an amount of 1 to 10 µg intramuscularly in one or several injections.

In another embodiment of this aspect of the invention, the method comprises administering the carrier molecule of the invention to an individual. Preferably, the response is a protective response. The amount of carrier molecule necessary for such an immunization can be determined by those of skill in the art without undue or excessive experimentation. For example, compositions comprising the carrier molecules of the invention can be administered in an amount of 40 to 100 µg intramuscularly, in one or several injections.

Thus, this aspect of the invention provides a method of DNA vaccination. The method also includes administering any combination of the chimeric nucleic acids, the chimeric polypeptides, and the carrier molecule of the invention to an individual. In embodiments, the individual is an animal, and is preferably a mammal. More preferably, the mammal is selected from the group consisting of a human, a dog, a cat, a bovine, a pig, and a horse. In an especially preferred embodiment, the mammal is a human.

The methods of treating include administering immunogenic compositions comprising polypeptides, but compositions comprising nucleic acids (including the carrier molecule) as well. Those of skill in the art are cognizant of the concept, application, and effectiveness of nucleic acid vaccines (e.g., DNA vaccines) and nucleic acid vaccine technology as well as protein and polypeptide based technologies. The nucleic acid based technology allows the administration of nucleic acids, naked or encapsulated, directly to tissues and cells without the need for production of encoded proteins prior to administration. The technology is based on the ability of these nucleic acids to be taken up by cells of the recipient organism and expressed to produce an immunogenic determinant to which the recipient's immune system responds. Typically, the expressed antigens are displayed on the cell surface of cells that have taken up and expressed the nucleic acids, but expression and export of the encoded antigens into the circulatory system of the recipient individual is also within the scope of the present invention. Such nucleic acid vaccine technology includes, but is not limited to, delivery of naked DNA and RNA, and delivery of expression vectors encoding polypeptides of interest (carrier molecules). Although the technology is termed "vaccine", it is equally applicable to immunogenic compositions that do not result in a protective response. Such non-protection inducing compositions and methods are encompassed within the present invention.

Although it is within the present invention to deliver nucleic acids and carrier molecules as naked nucleic acid, the present invention also encompasses delivery of nucleic acids as part of larger or more complex compositions. Included among these delivery systems are viruses, virus-like particles, or bacteria containing the chimeric nucleic acid or carrier molecule of the invention. Also, complexes of the invention's nucleic acids and carrier molecules with cell permeabilizing compounds, such as liposomes, are included within the scope of the invention. Other compounds, supra molecular vectors (EP 696,191, Samain et al.) and delivery systems for nucleic acid vaccines are known to the skilled artisan, and exemplified in WO 90 111 092 and WO 93 06223 (Vical's patents), and can be made and used without undue or excessive experimentation.

The methods of treating individuals according to the invention include prophylactic treatment, therapeutic treatment, and curative treatment. Prophylactic treatment is treatment of an individual, using the methods of the invention, before any clinical sign of disease or infection is identified. Thus, prophylactic treatment is a preventative treatment and includes vaccination. Prophylactic treatment also includes treatment that is instituted after actual infection or disease inception, but before at least one clinical sign of the disease or infection is observed. Therapeutic treatment is treatment of an individual after at least one clinical sign of disease or infection is identified, or after an individual is known to (or is highly suspected of) having been exposed to a quantity of an agent that sufficient to cause disease or infection. Therapeutic treatment methods do not necessarily result in elimination of the disease or infection; however they do provide a clinically detectable improvement in at least one clinical sign of the disease or infection. Curative treatment methods result in complete elimination of the clinical signs of the disease or infection in the treated individual. Included in the curative treatment methods are those that result in complete removal of the causative agent of the infection or disease, whether it be a virus, bacterium, or host cell (such as a cancerous cell). Also included in curative treatment methods are those that cause complete remission of a disease, i.e. complete elimination of all outward clinical signs of infection or disease, and repression of all detectable clinical manifestations of the infection or disease.

With respect to rabies vaccination, it is known that the virus can be treated both prophylactically (e.g., by vaccination of dogs) and curatively (e.g., by a series of injections to a human previously bitten by a rabid dog). Thus, a preferred embodiment of the present invention is a method of vaccinating an individual with a vaccine comprising the immunogenic composition of the invention. As discussed above, the immunogenic composition of the invention can comprise (or encode) multiple antigenic determinants. Therefore, a method of the invention can include multiple types of treatment for multiple types of diseases or infections. For example, a single method of treatment can comprise prophylactic treatment of polio, prophylactic and therapeutic treatment of rabies, and prophylactic treatment of influenza.

It will be apparent to those of ordinary skill in the art that various modifications and variations can be made in the construction of the molecules, and practice of the methods of the invention without departing from the scope or spirit of the invention. The invention will now be described in more detail with reference to specific examples of the invention, which are not intended to be, and should not be construed as, limiting the scope of the invention in any way.

BRIEF DESCRIPTION OF THE DRAWINGS AND TABLES

The invention will be described in greater detail with reference to the drawings, in which:

FIG. 1 depicts *lyssavirus* glycoproteins and chimeric constructs of *lyssavirus* glycoproteins. SP—Signal peptide; TM—Transmembrane domain; $S_1$—NL amino acid residues; $S_2$—NS amino acid residues; $S_3$— LFAV amino acid residues.

(A) Schematic representation of *lyssavirus* PV glycoprotein (G), indicating regions encompassing site II, site III, and epitopes I, V, and VI, as well as the transmembrane domain (TM) is presented at the top. Chimeric polypeptides are schematically depicted on the other lines, with deletion and/or fusion points indicated by residue numbers. Numbers are the positions of amino acid residues on the mature protein (signal peptide cleaved).

(B) Amino acid sequences of the chimeric polypeptides at the fusion sites, PV-PV (SEQ ID NO: 18); -PVIII (SEQ ID NO: 19); ELBI-PV (SEQ ID NO: 20); MoK-PV (SEQ ID NO: 21); PV-MoK (SEQ ID NO: 22); MoK-Sad (SEQ ID NO: 23). The linear region carrying epitope VI (amino acid 264) is indicated by underlining at residues 251–275. Black and gray boxes outline the EBL-1 and Mok sequences, respectively. Dashes represent amino acids similar to those of the PV sequence, and dots correspond to gaps.

(C) Schematic representation of the inserted sequences encoding the C3 poliovirus epitope involved in virus neutralizing antibody induction (B), and lymphocytic choriomeningitis virus (LCMV) nucleoprotein CD8H-$2^d$ (CTL) cell epitope involved in the induction of both cytotoxic T Lymphocytes (CTL) and protection against LCMV challenge in the truncated (GPVIII) and chimeric *lyssavirus* G protein (GEBL1-PV).

(D) Putative PEST sequence analysis around the junction of the end of EBL1 part and the beginning of B cell epitope is also reported.

(E) Comparison of the deduced amino acid sequences of G proteins of selected *lyssaviruses*, PV (SEQ ID NO: 24); USA7-BT (SEQ ID NO: 25); PI (SEQ ID NO: 26); EBLI-POL (SEQ ID NO: 27); EBLIFRA (SEQ ID NO: 28); EBL2FIN (SEQ ID NO: 29); EBL2HOL (SEQ ID NO: 30); Duv1SAF (SEQ ID NO: 31); Duv2SAF (SEQ ID NO: 32); Lag1NGA (SEQ ID NO: 33); Lag2CAR (SEQ ID NO: 34); MoK3ETP (SEQ ID NO: 35); MoK2ZIM (SEQ ID NO: 36). The consensus sequence is presented as the bottom sequence. Light grey boxes indicate the main antigenic sites. Dark grey boxes indicate the hydrophobic signal peptide (SP) and the transmembrane domain (TM). Underlined NX(S/T) motifs are potential N-glycosylation sites.

Figure 2:
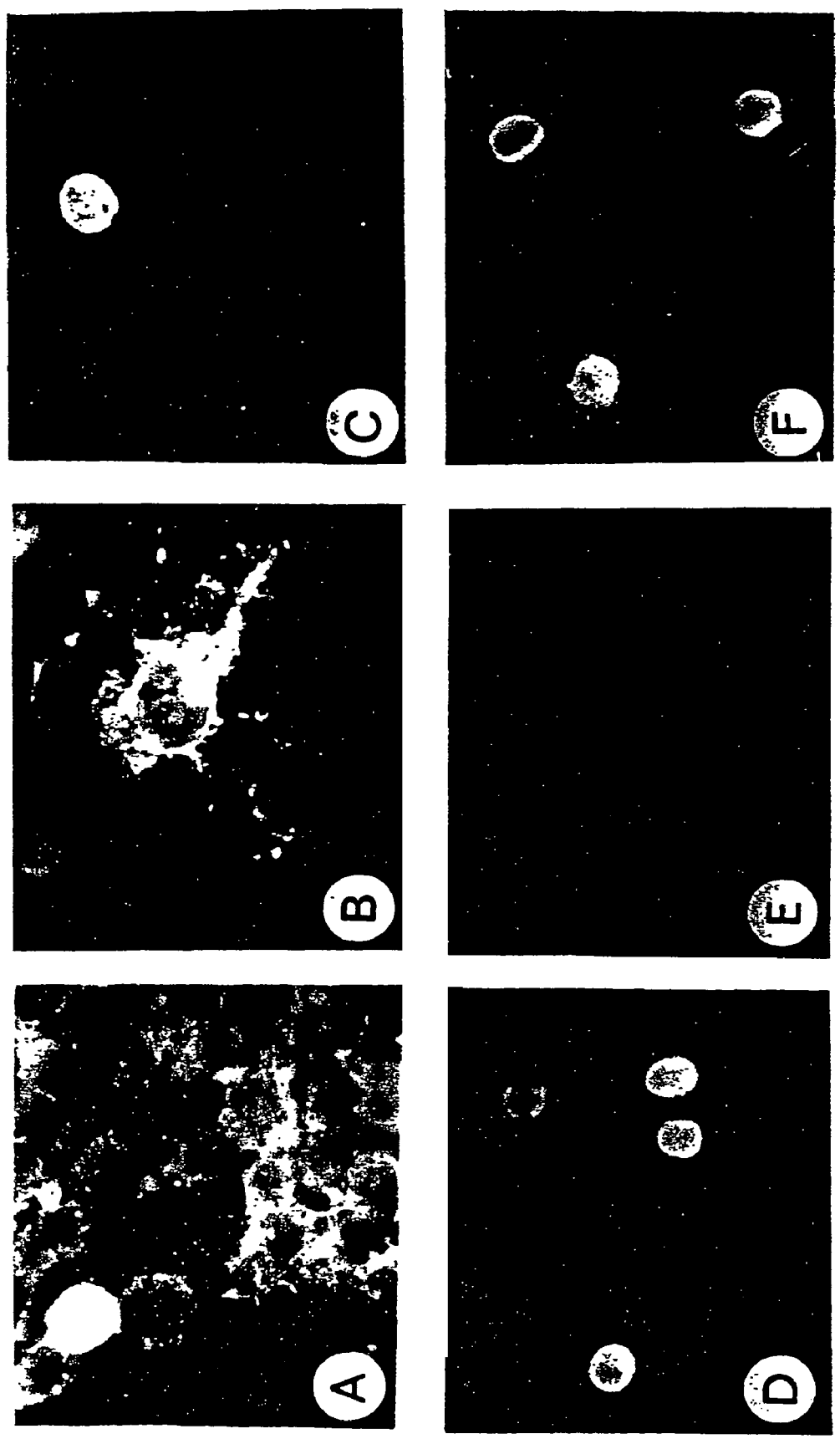
Figure 2:
Figure 2:
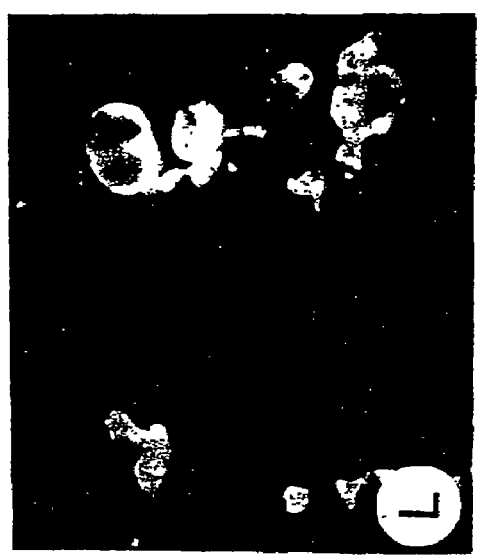
Figure 2:
Figure 2:
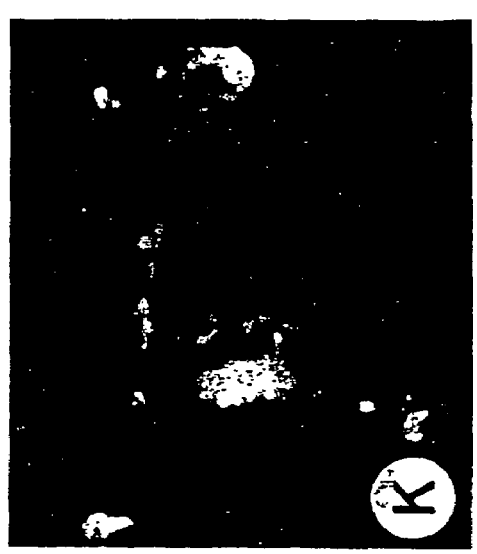
Figure 2:
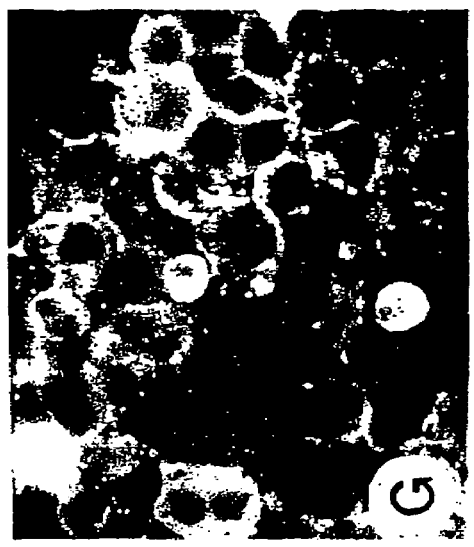
Figure 2:
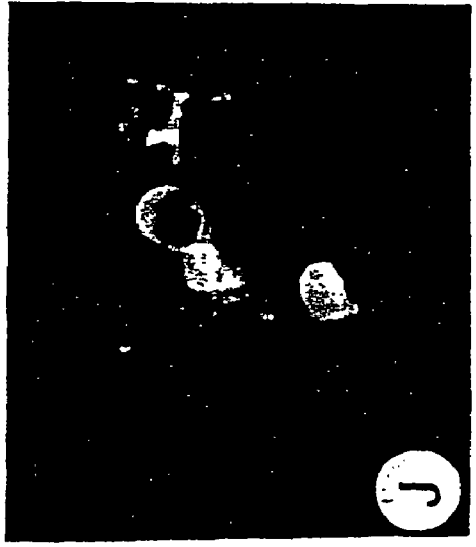
Figure 2:
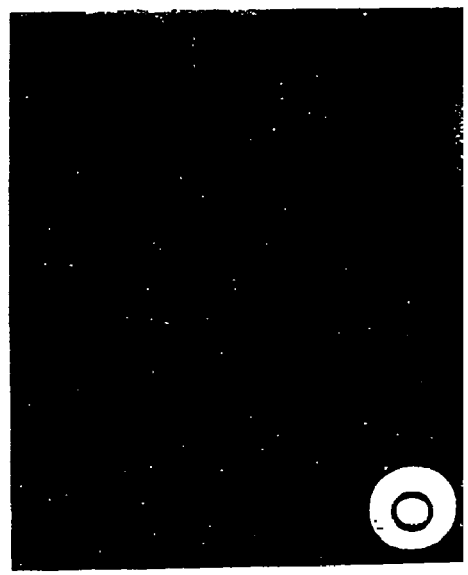
Figure 2:
Figure 2:

FIG. 2 shows indirect immunofluorescence microscopy of *lyssavirus* G production in Neuro-2a cells 48 h after transient transfection with various plasmids: pGPV-PV (A, B and C), pG-PVIII (D, E and F), pGEBL1-PV (G, H, and I), pGMok-PV (J, K and L), and pGPV-Mok (M, N and O). Forty eight hours after transfection, cells were permeabilized and stained with antibodies: anti-PV G PAb (A, D, G, J and M), PV D1 anti-native PV G site III MAb (B, E, H and K), 6B1 anti-denatured G site III MAb 8 and F), anti-EBL-1 G Pab (I), anti-Mok G PAb (L and N) and serum from an unimmunized mouse (0).

Figure 3:
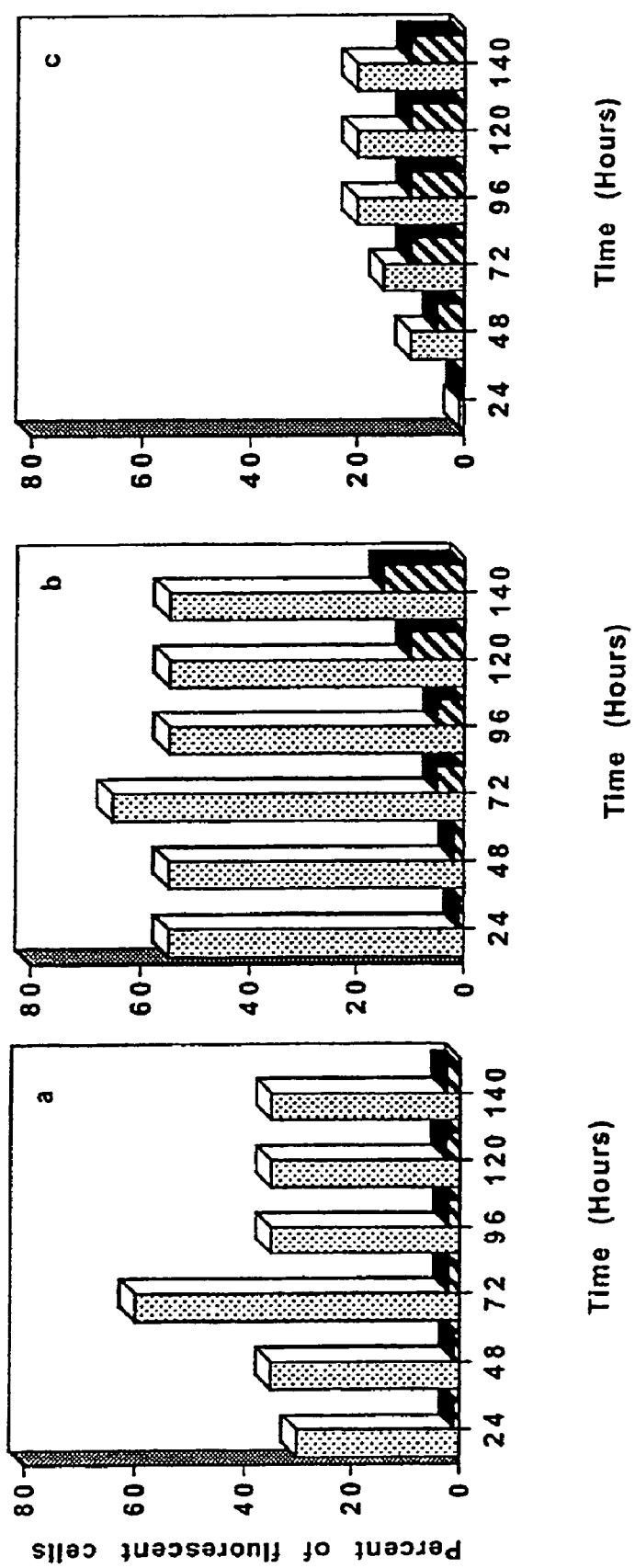

FIG. 3 shows the results of a kinetic study of antigen synthesis in Neuro-2a cells transiently transfected with pGPV-PV (a), pGEBL1-PV (b) or pG-PVIII (c). Cells were permeabilized at various times and stained with PV PAb (dotted bar) or anti-denatured G site III 6B1 MAb (hatched bar).

Figure 4:
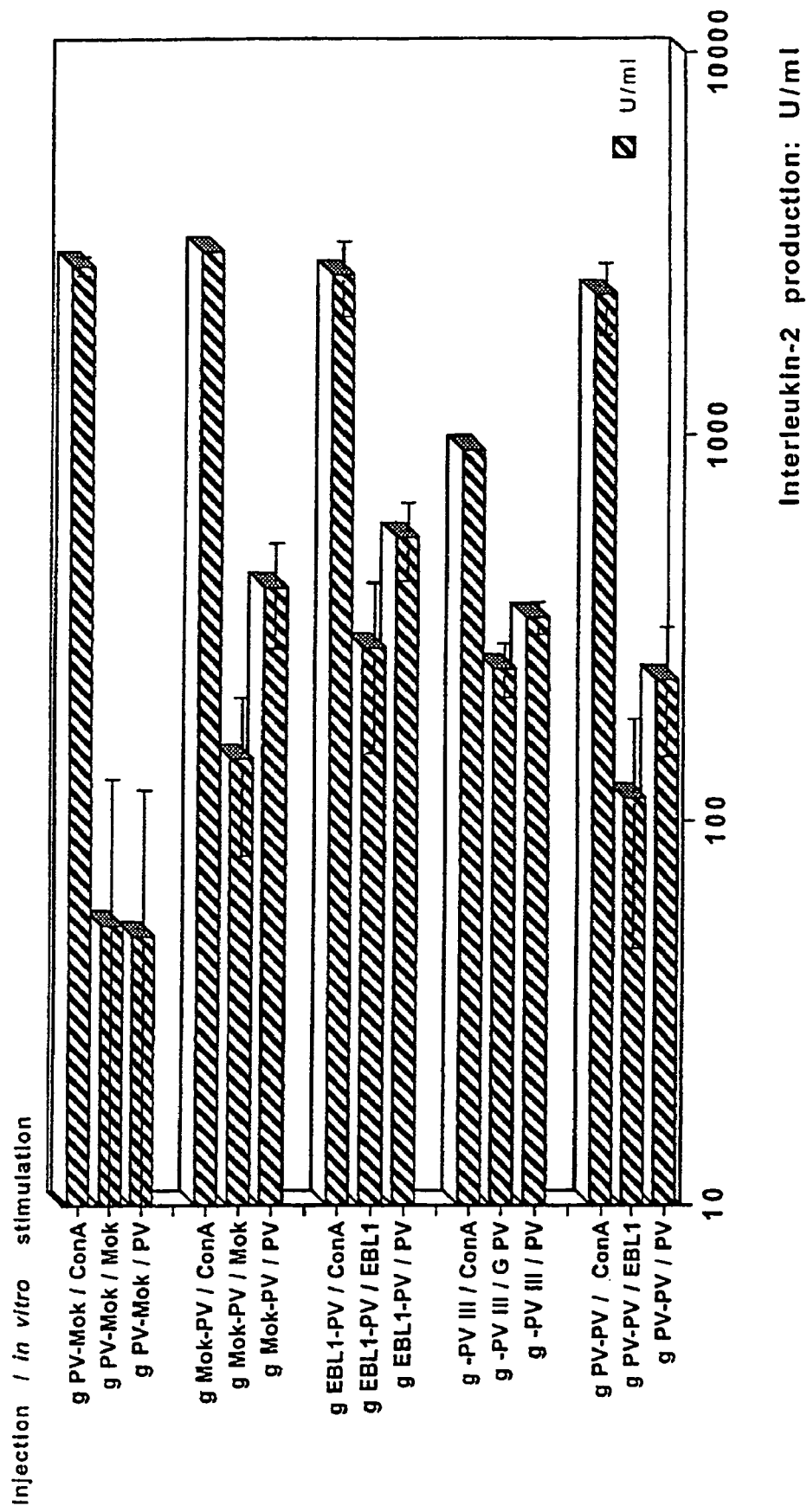

FIG. 4 shows the results of induction of IL-2-producing cells by plasmids encoding various *lyssavirus* G. BALB/c mice (two animals for each plasmids) were injected i.m. (50 µl in each anterior tibialis muscle) with 40 µg plasmid (pGPV-PV, pG-PVIII, pGEBL1-PV, pGMok-PV and pGPV-Mok). Spleens were removed 21 days later and splenocytes were specifically stimulated in vitro by inactivated and purified viruses (PV, EBL1 or Mok), G PV, or polyclonally stimulated by concanavalin A (ConA). The amount of IL-2 released was then assayed in triplicates by bioassay and titers expressed as U/ml.

Figure 5:
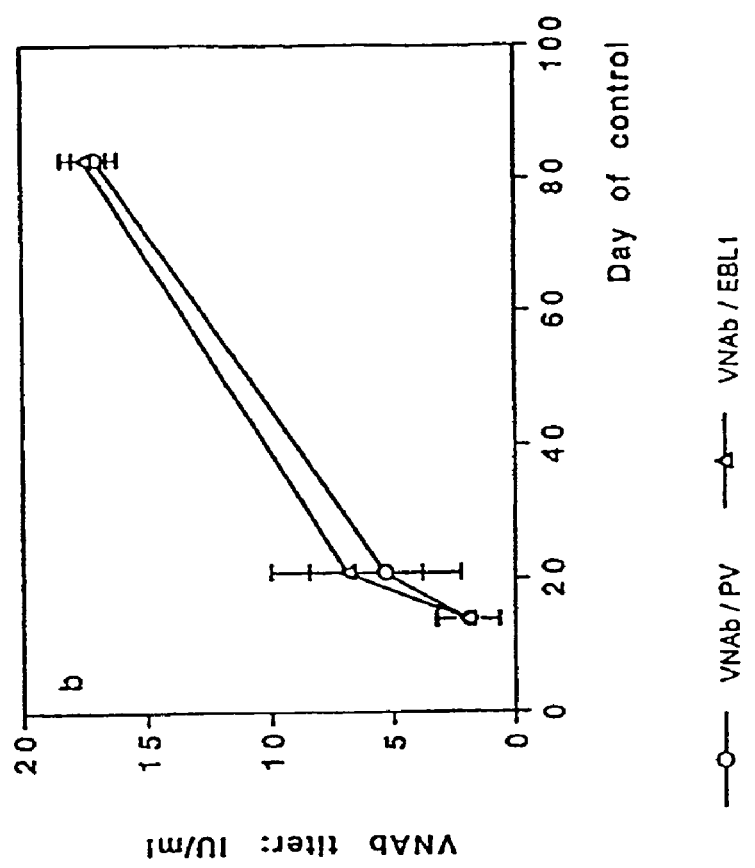
Figure 5:
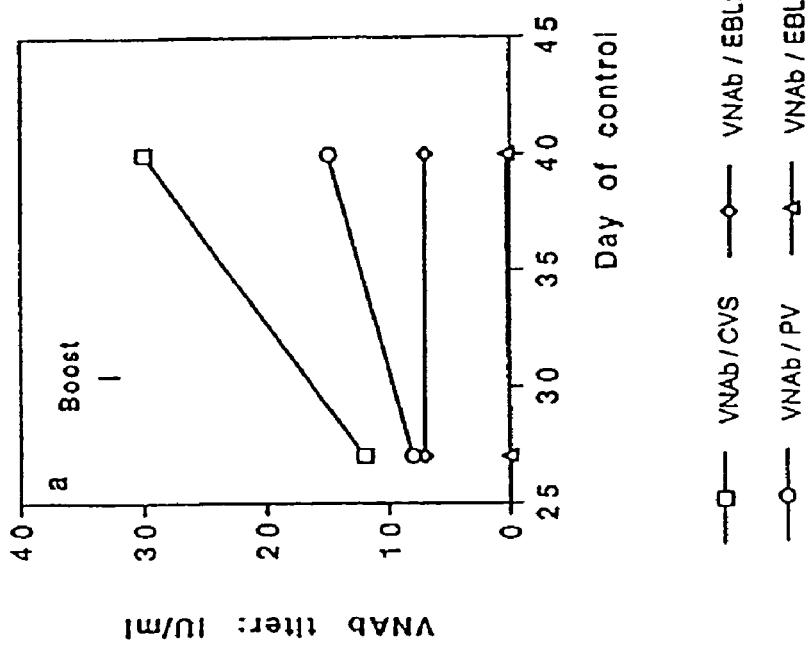

FIG. 5 shows induction of VNAb against European *lyssavirus* genotypes by plasmid. BALB/c mice were injected with 40 µg plasmid in the tibialis muscle.

(A) Injection with pGPV-PV. Mice received a boost on day 30. Sera (pool of 3 samples) were assayed on days 27 and 40 for VNAb against viruses of genotypes 1 (CVS and PV), 5 (EBL1b), and 6 (EBL2b).

(B) Injection with pGEBL1-PV. Four mice received only one injection of plasmid and blood samples were collected at various intervals by trans-orbital puncture. Sera were assayed by RFFIT using PV and EBL1 b viruses for VNAb determination.

Figure 6:
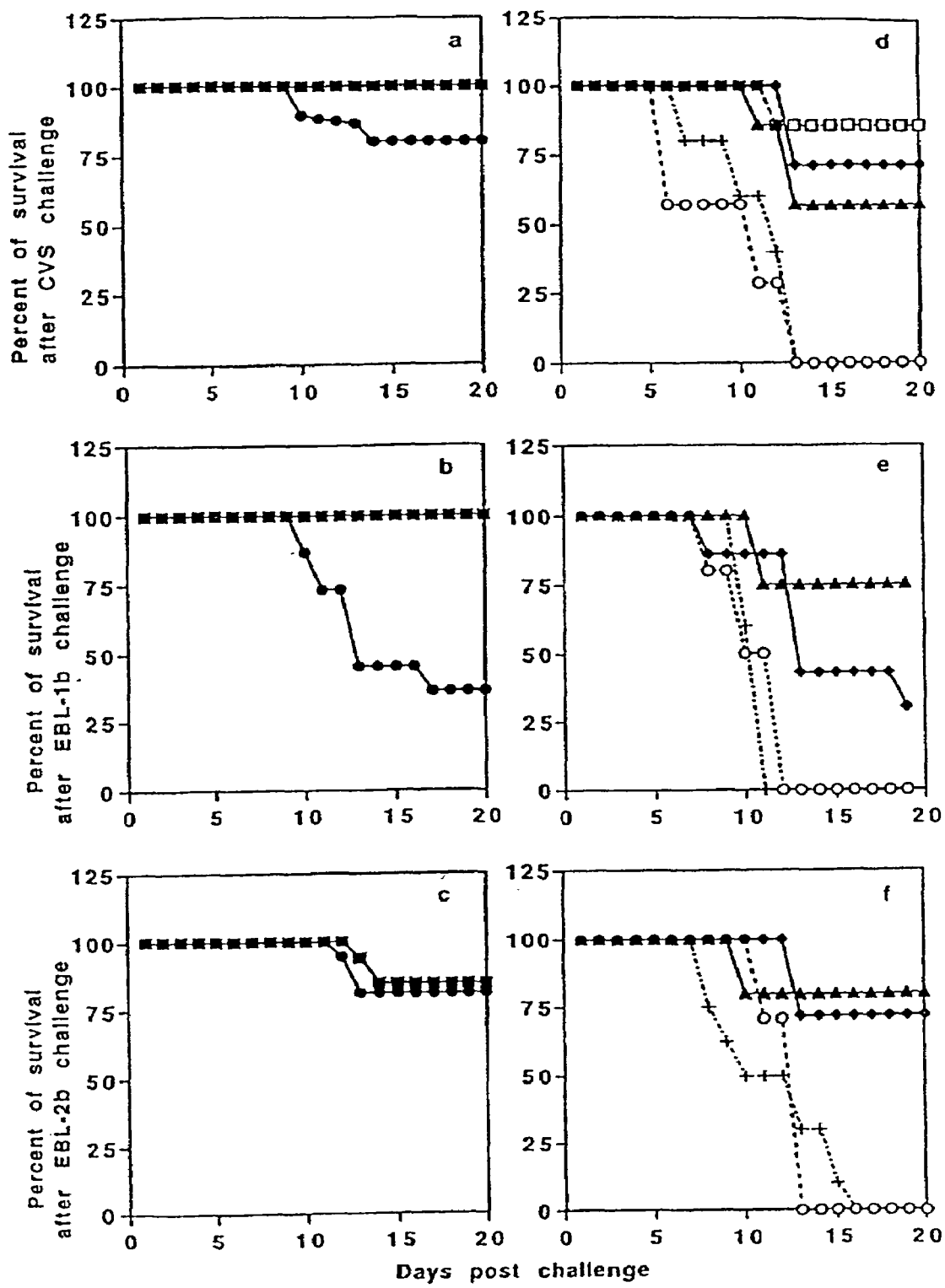

FIG. 6 shows comparative protection induced by pGPV-PV, pGEBL1-PV plasmids, and rabies PM and PV vaccines against CVS, EBL-1b, and EBL-2b. BALB/c mice (9 animals per series) were injected i.p. on days 0 and 7 with 0.5 ml of PM vaccine diluted 1/10th (solid circles) or with 2 µg of inactivated and purified PV virus (solid squares). For DNA-based immunizations, BALB/c mice (5 animals for each plasmid) were injected in the tibialis muscle with PBS (open circles) or with 40 µg of various plasmids pGPV-PV (diamond), EBL1-PV (solid triangle), pClneo backbone (cross). Swiss mice (6 animals) were injected with pGPV-PV (open square).

(a) Inactivated virus was injected. BALB/c and Swiss mice were challenged i.c. on day 21 with about 30 $LD_{50}$ of CVS.

(b) Inactivated virus was injected. BALB/c and Swiss mice were challenged i.c. on day 21 with about 30 $LD_{50}$ of EBL-1b.

(c) Inactivated virus was injected. BALB/c and Swiss mice were challenged i.c. on day 21 with about 30 $LD_{50}$ of EBL-2b.

(d) DNA was injected. BALB/c and Swiss mice were challenged i.c. on day 21 with about 30 $LD_{50}$ of CVS.

(e) DNA was injected. BALB/c and Swiss mice were challenged i.c. on day 21 with about 30 $LD_{50}$ of EBL-1b.

(f) DNA was injected. BALB/c and Swiss mice were challenged i.c. on day 21 with about 30 $LD_{50}$ of EBL-2b.

Figure 7:
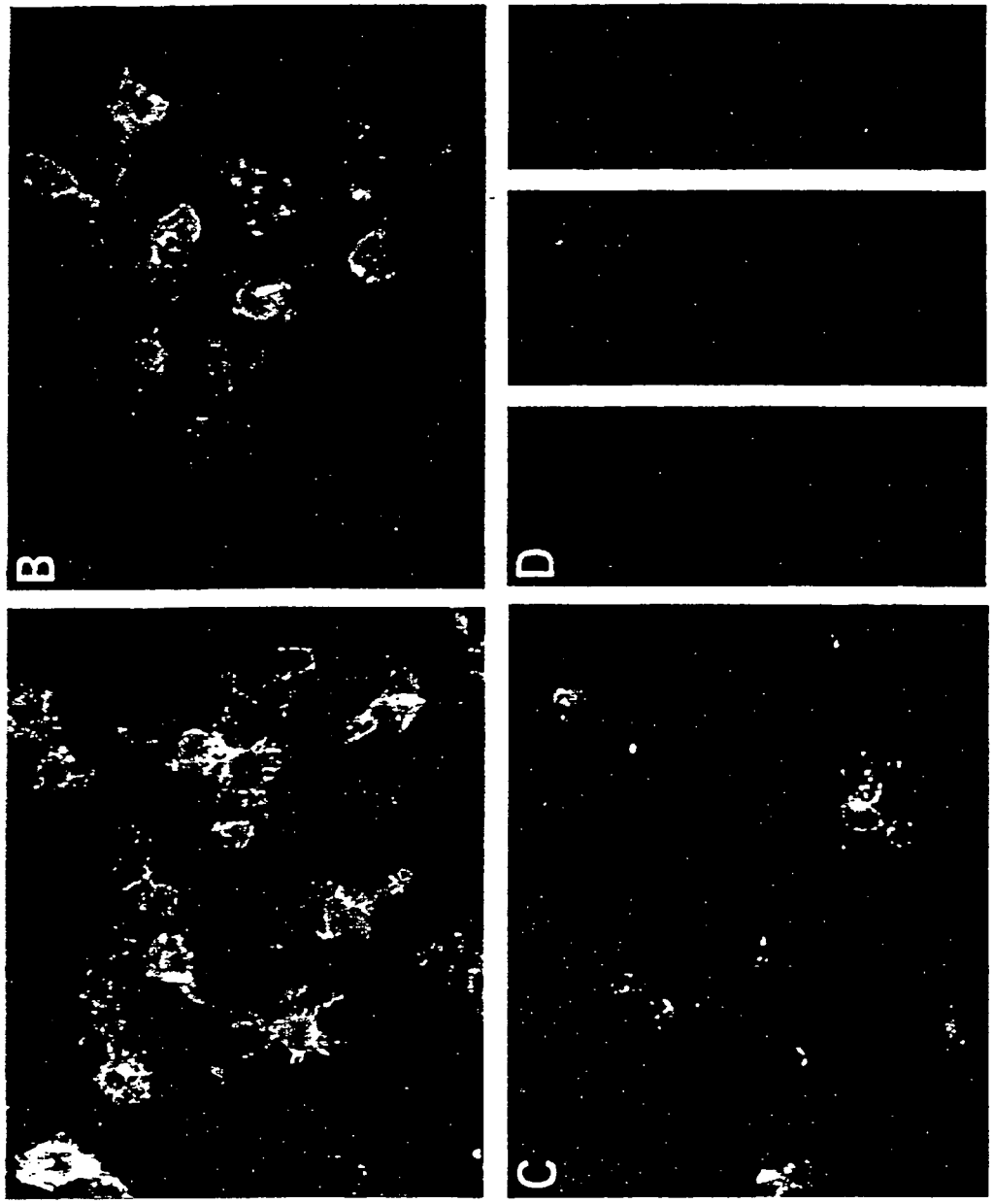

FIG. 7 shows indirect immunofluorescence microscopy of antigens expressed in Neuro-2a cells transfected with plasmids.

(A) Cells were transfected with plasmid pGEBL1-(B-CTL)$_2$-PV and stained with the rabies D1 MAb.

(B) Cells were transfected with plasmid pGEBL1-(B-CTL)$_2$-PV and stained with the poliovirus C3 MAb.

(C) Cells were transfected with plasmid pGEBL1-(B-CTL)$_2$-PV and stained with the antipoliovirus type 1 PAb.

(D) Cells were transfected with plasmid pClneo and stained with either 1) the rabies D1 Mab, 2) the poliovirus C3 MAb, or 3) the antipoliovirus type 1 PAb.

Figure 8:
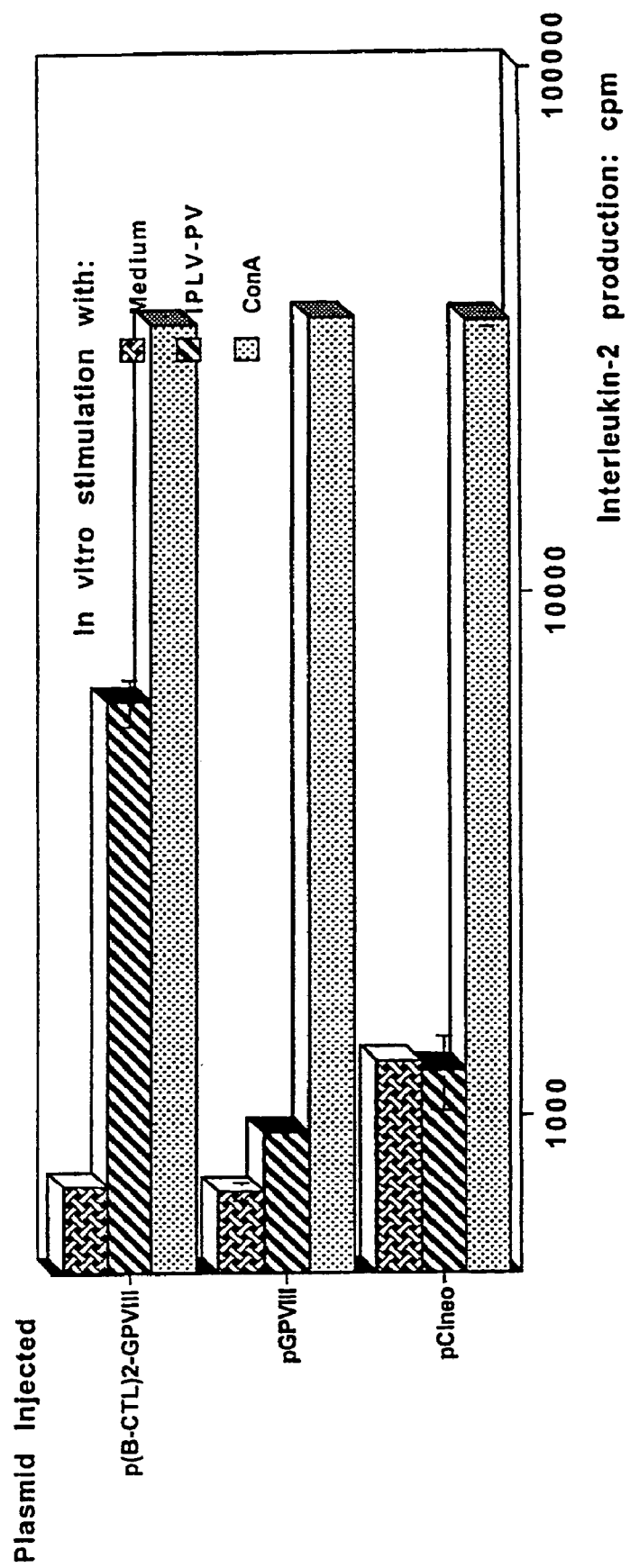
Figure 8:
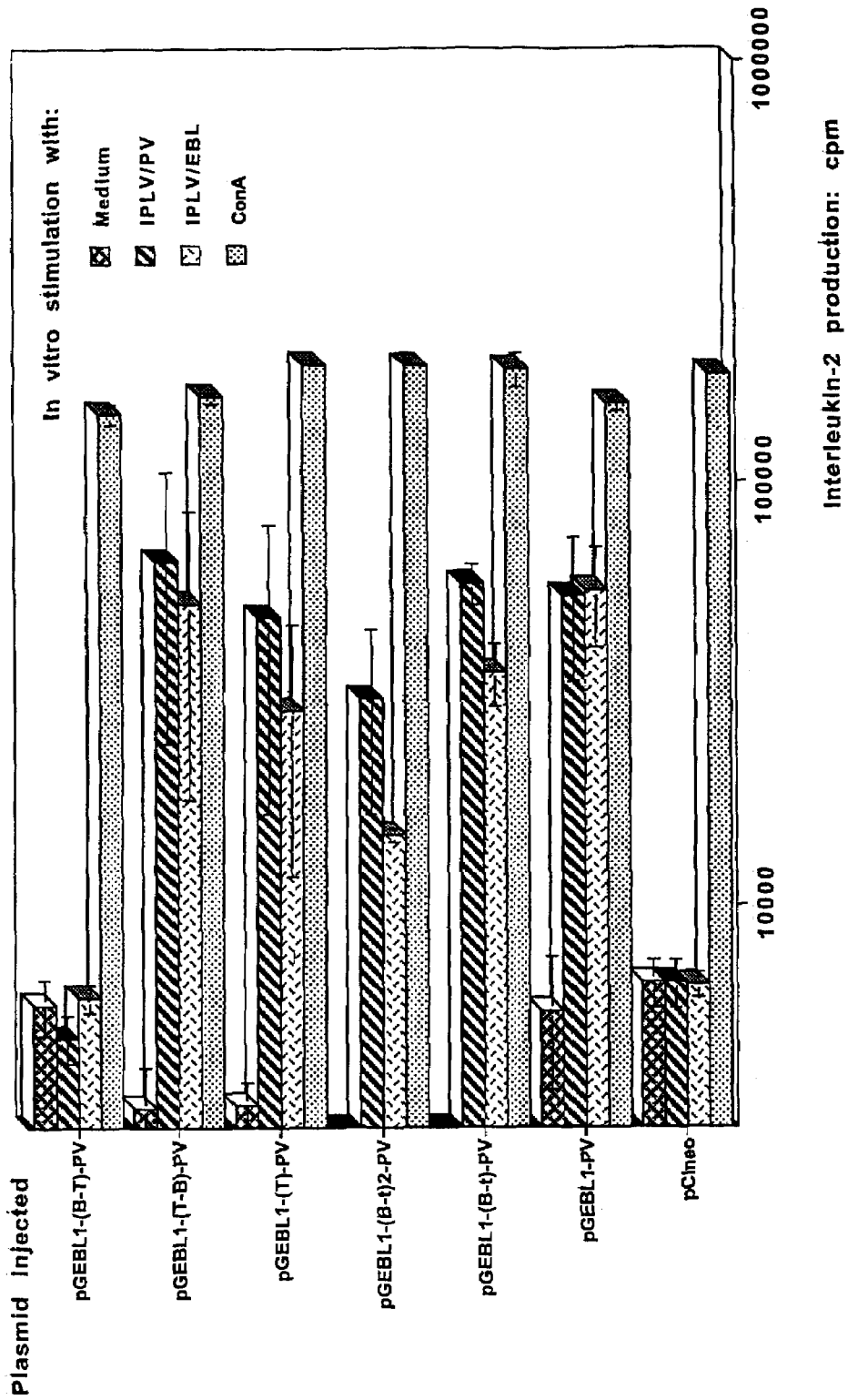

FIG. 8 shows induction of IL2-producing cells by pGPVIII (A) or pGEBL1-PV (B) carrying poliovirus and LCMV epitopes. BALB/c mice (two animals for each plasmids) were injected i.m. (50 μg in each anterior tibialis muscle) with plasmids. Spleens were removed 14 days later and splenocytes were stimulated in vitro by cell culture medium (crossed bar) specifically by inactivated and purified *lyssaviruses* (IPLV PV: hashed bar; IPLV EBL: light hatches) or polyclonally stimulated by ConA (dotted bar). The amount of IL-2 released was then assayed in triplicates by bioassay and titers expressed as U/ml.

(A) Plasmids injected were pClneo-empty plasmid-, pGPVIII, and p(B-CTL)$_2$-GPVIII.

(B) Plasmids injected were pClneo, pGEBL1-PV, pGEBL1-(B)-PV, pGEBL1-(CTL)-PV, pGEBL1-(CTL-B)-PV, pGEBL1-(B-CTL)$_2$-PV.

Figure 9:
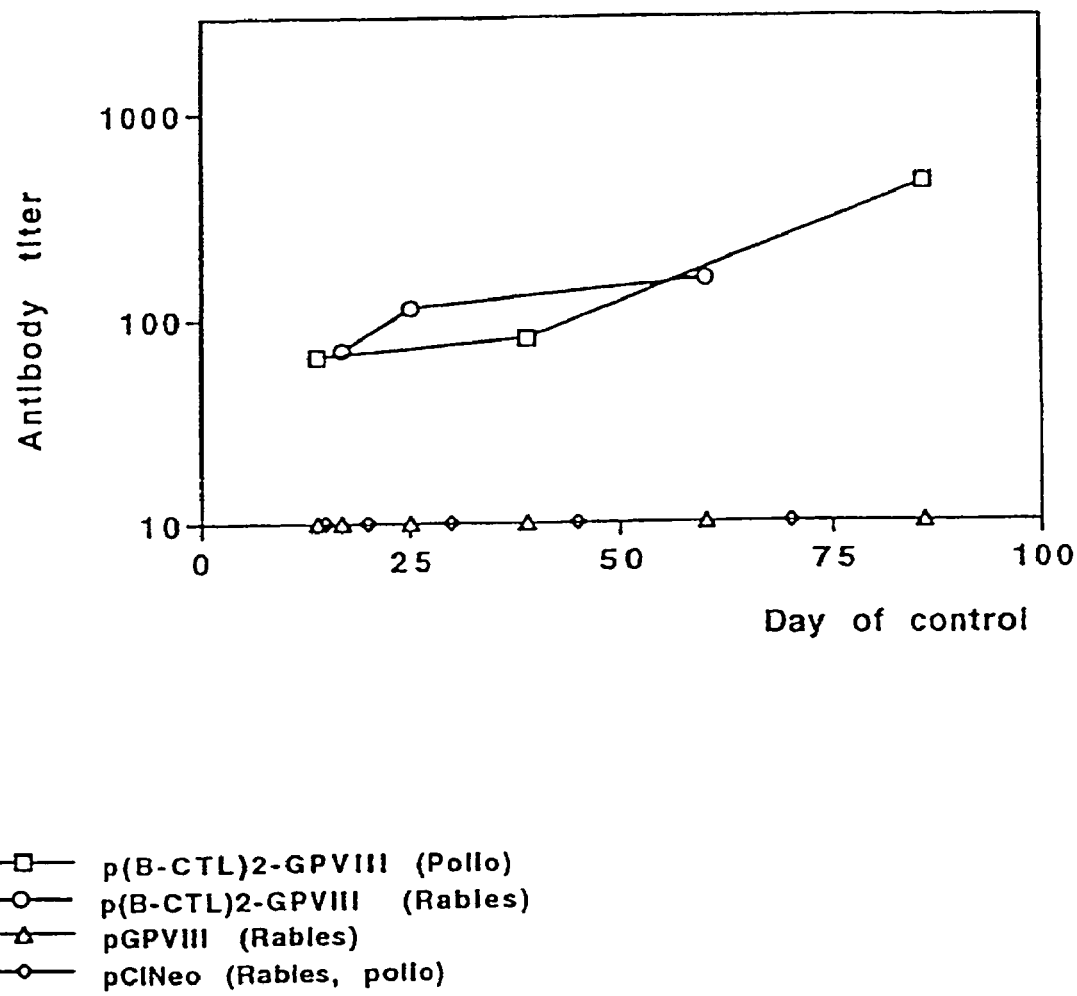

FIG. 9 shows a kinetic study in BALB/c mice of antibody production induced by p(B-CTL)2-GPVIII or pGPVIII against poliovirus peptide and rabies virus. Three mice were injected with 40 μg of p(B-CTL)2-GPVIII (square and circle), or pGPVIII (triangle), or empty pClneo (diamond). After puncture by retro-orbital route at various times, sera were assayed by ELISA for the determination of antibody against poliovirus peptide (square and diamond) or rabies virus (circle, triangle and diamond).

Figure 10:
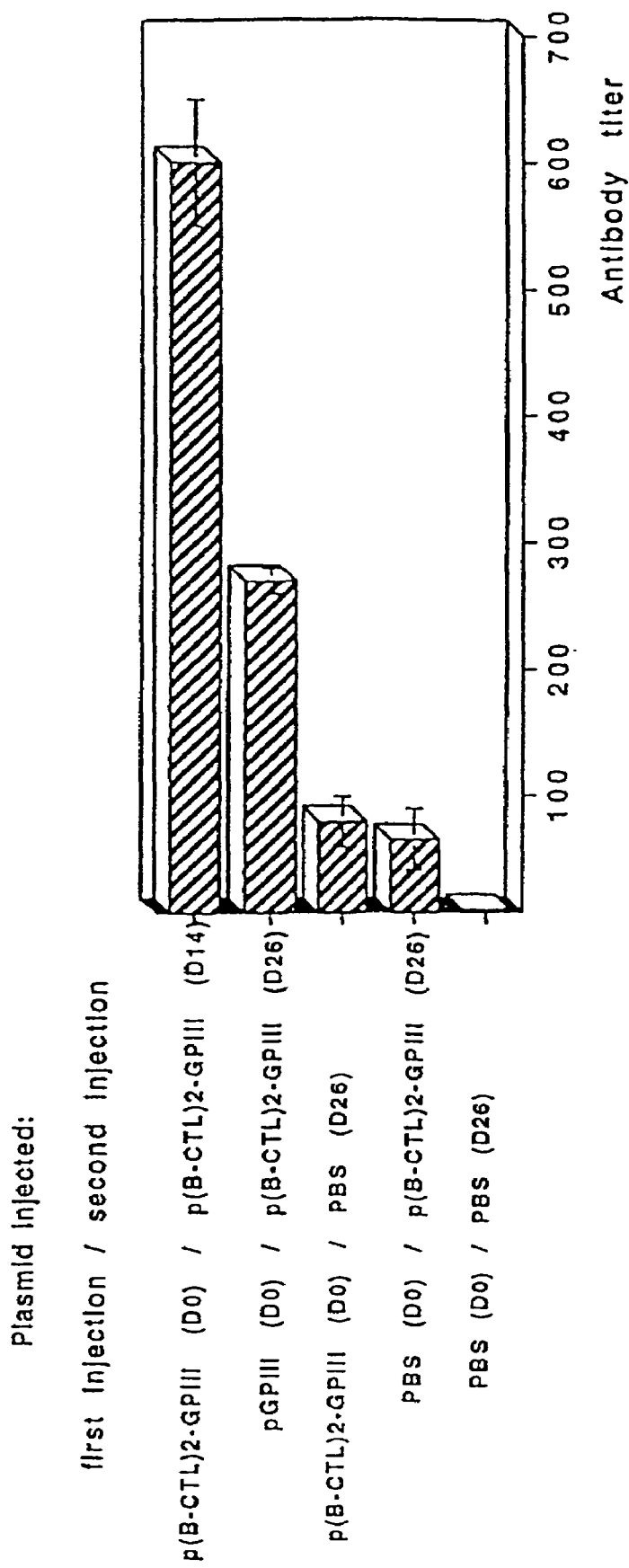

FIG. 10 shows the influence of a priming on the poliovirus antipeptide antibody production induced by p(B-CTL)2-GPVIII. Five groups of three mice received on day 0 PBS (2 groups), p(B-CTL)2-GPVIII (2 groups), or pPVIII. One group (injected with p(B-CTL)2-GPVIII) was not boosted, whereas the group injected with pPVIII was boosted with p(B-CTL)2-GPVIII on day 26. One group (injected with p(B-CTL)2-GPVIII) was boosted with p(B-CTL)2-GPVIII on day 14. All animals were controlled for antipeptide antibody production on day 39 by ELISA.

Figure 11:
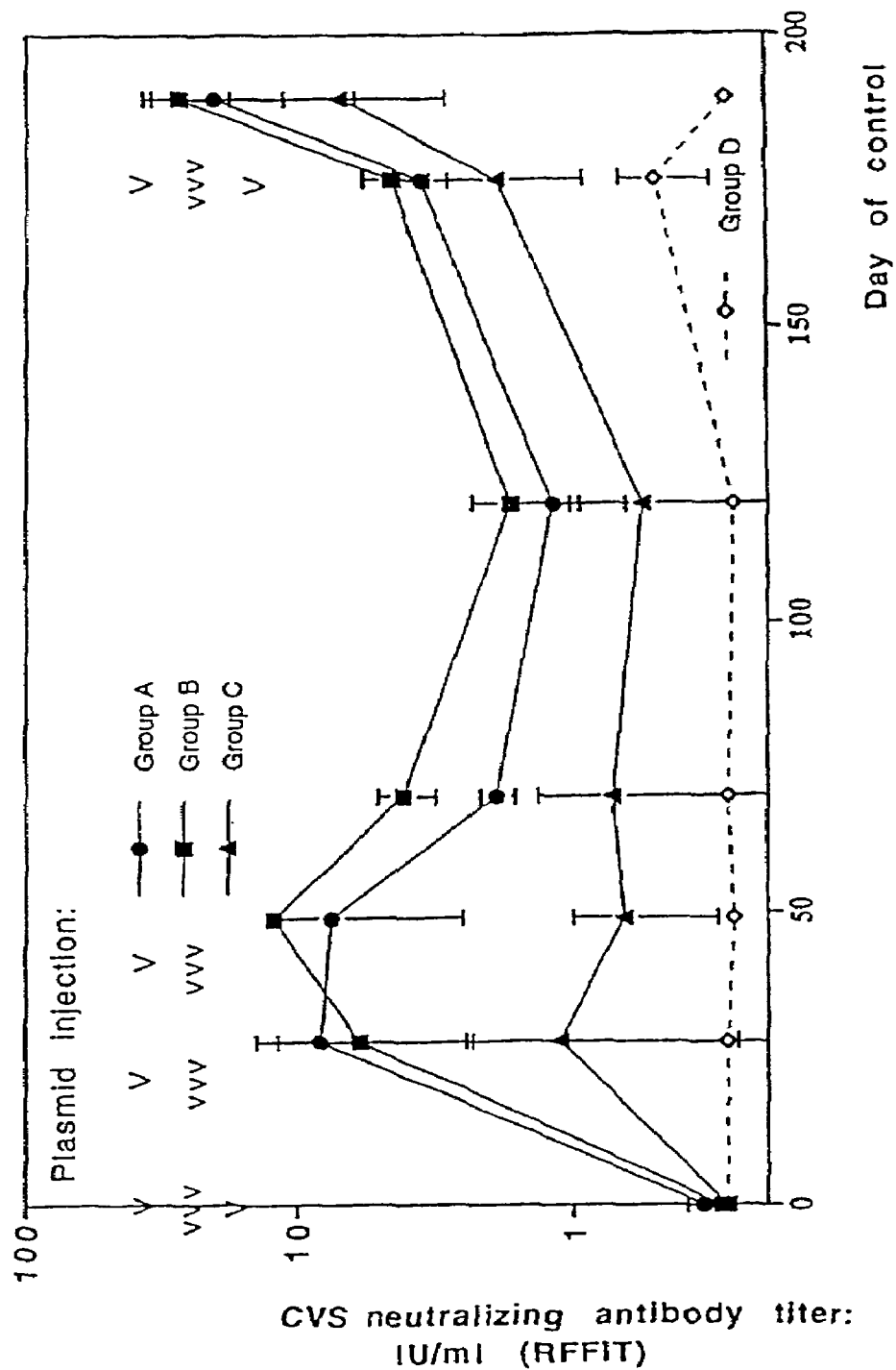

FIG. 11 shows the production of rabies virus neutralizing antibodies against the challenge virus standard (EVS) after injection of the full homogeneous plasmid pGPV in beagle dogs.

Group A: Injection of 100 μg of plasmid in one site on days, 0, 21, 42, and 175.

Group B: Injection of 33 μg of plasmid in three sites on days 0, 21, 42, and 175.

Group C: Injection of 100 μg of plasmid in one site on days 0 and 175.

Group D: Injection of phosphate buffered saline (control).

Figure 12:
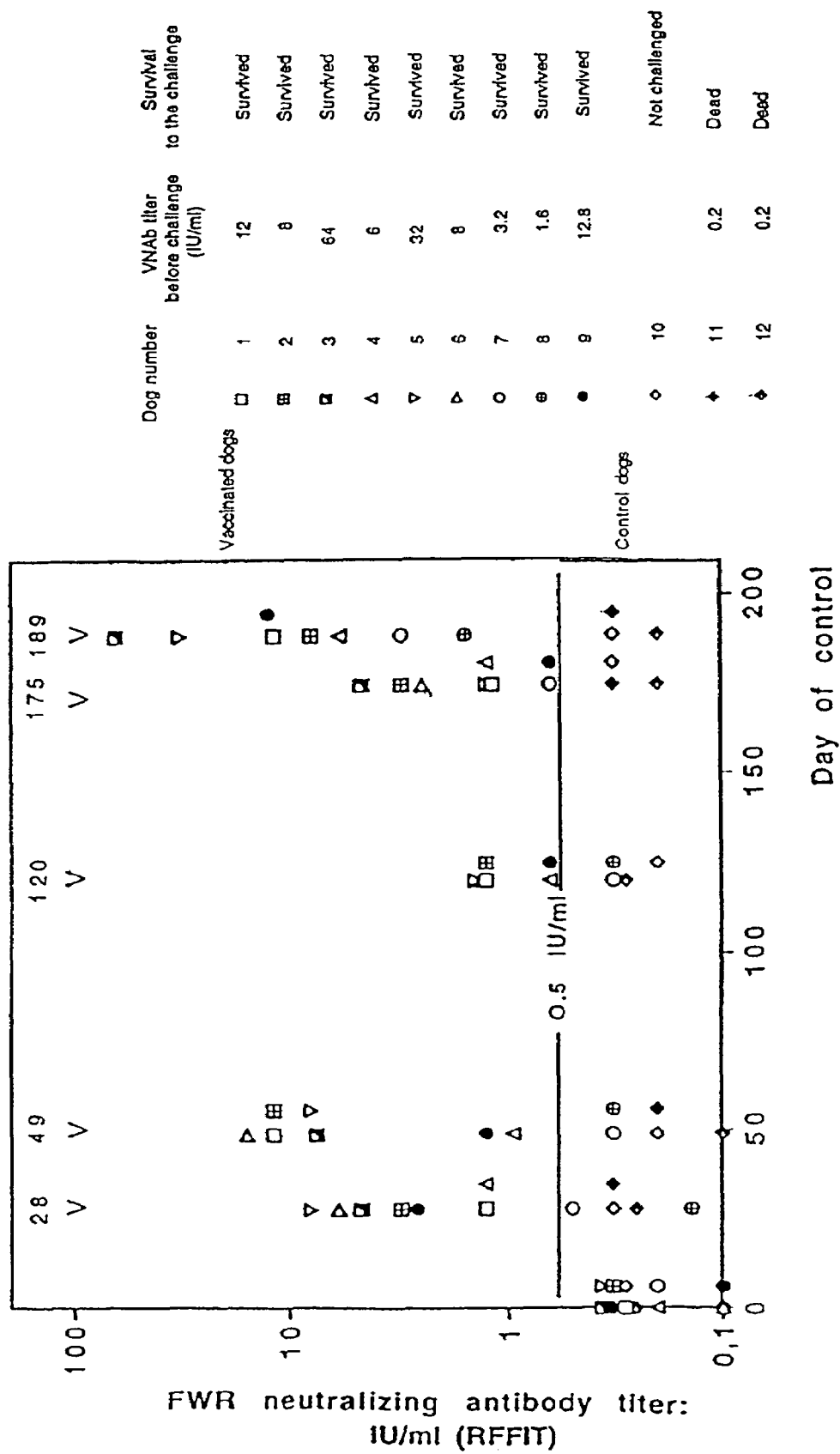

FIG. 12 shows individual neutralizing antibody response against a wild rabies virus (fox form France, fox wild rabies virus FWR) after injection of the full homogeneous plasmid pGPV in beagle dogs. It shows also the protection induced against an intramuscular challenge performed on day 175 with a wild rabies virus isolated from rabid dogs.

Figure 13:
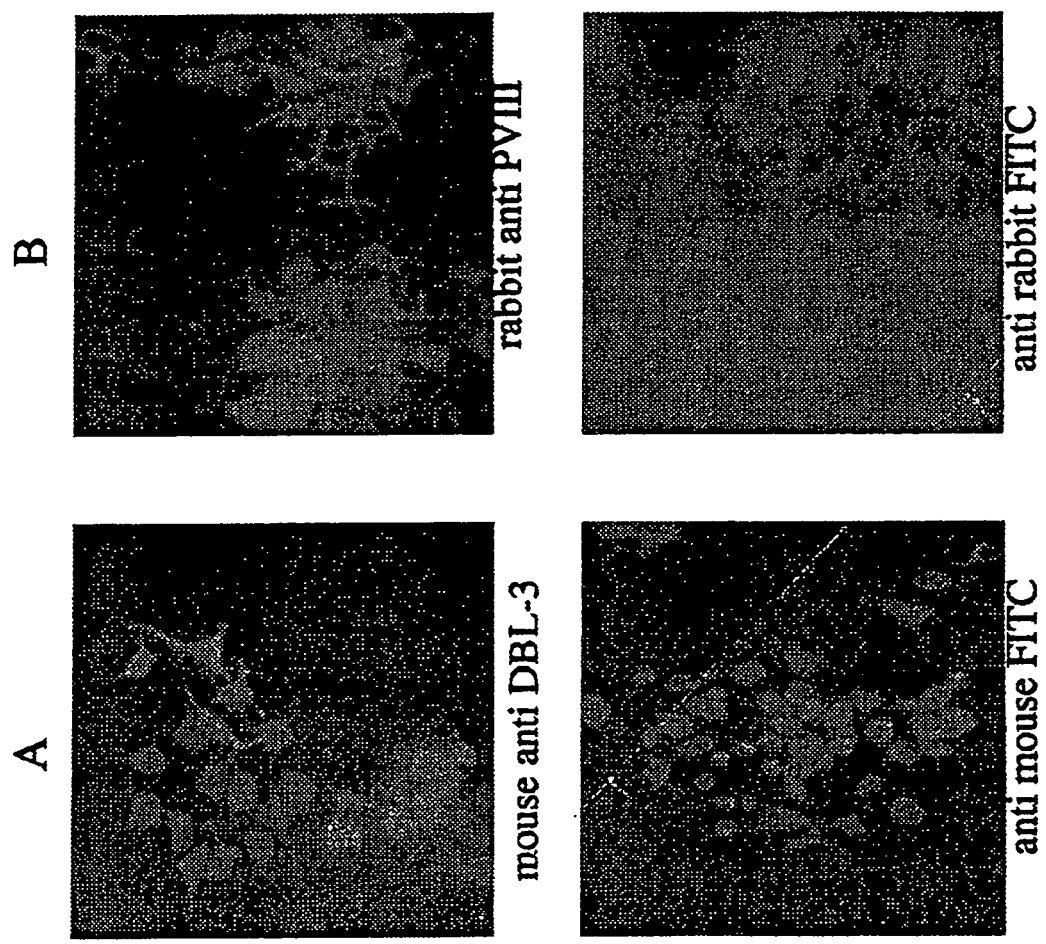

Dogs nos. 1 to 3=group A
Dogs nos. 4 to 6=group B
Dogs nos. 7 to 9=group C
Dogs nos. 10 to 12=group D FIG. 13 shows N2A cells transfected with the plasmid DBL-3/PVIII (Fugene, Roche Molecular Biochemicals) and fixed with Acetone (80%) for 10 min. on ice. A.) Mouse anti DBL-3 GST fusion protein (1/1000 dilution). B.) Rabbit anti PVIII (1/400 dilution). Background reactivities seen with the second antibody conjugated to FITC are shown. This figure clearly shows that both DBL-3 and PVIII regions were efficiently expressed at the membrane of the transfected cells.

EXAMPLES

For the Examples, the following materials and methods were used, unless otherwise specifically stated.

Mice. Female BALB/c (H-2$^d$ BALB/C), 6 to 8 weeks of age and Swiss (14 to 16 g) mice were purchased from "Centre d'Elevage et de Recherche" Janvier (Legenest St Isle, France).

Cells and *lyssaviruses*. BHK-21 cells used for the production and titration of *lyssaviruses* were grown in Eagle's minimal essential medium (MEM) containing 5% fetal bovine serum (FBS) and 5% new born calf serum (Perrin, P., 1996, "Techniques for the preparation of rabies conjugates", In *Laboratory techniques in rabies*, Meslin, F-X., Kaplan, M., and Koprowski, H. Eds., (WHO Geneva).:433–445). Neuroblastoma cells (Neuro-2a) used for transfection studies with plasmids were grown in MEM containing 8% FBS.

The interleukin-2 (IL-2)-dependent cytotoxic T cell line (CTLL) was cultured as previously described (Perrin, P. et al., 1988, "Interleukin-2 increases protection against experimental rabies", *Immunobiol.* 177:199–209) in RPMI-1640 medium (Gibco: Flowbio, Courbevoie, France) containing 10% FBS, 1 mM sodium pyruvate, 1 mM non-essential amino acids, $5\times10^{-5}$ M 2-mercaptoethanol, HEPES buffer (Flow Laboratories, Bethesda, USA) and 5 to 10 units (for $1\times10^4$ cells) of rat IL-2 (supernatant of splenocytes stimulated with concanavilin A: Con A). Cells were incubated at 37EC in a humidified atmosphere containing 7.5% $CO_2$.

Fixed PV-Paris/BHK-21, CVS rabies strains as well as rabies-related virus strains (EBL1b, EBL2b, LCMV, and Mok) were multiplied (passaged) in BHK-21 cells as previously described by Perrin, P., 1996, supra. The European bat *lyssaviruses* used were EBL1b (strain number 8916FRA) derived from a bat isolate from France and EBL2b (strain number 9007FIN; a gift from H. Bouhry) isolated from a human in Finland (Amengal, B. et al., 1997, "Evolution of European bat *lyssaviruses*", *J. Gen. Virol.* 78:2319–2328). The LCMV strain Arm/53b was kindly provided by Drs. M. Oldstone and M. McChesney (Scripps Clinic, La Jolla, Calif.).

Rabies virus antigens and vaccines. Inactivated and purified *lyssaviruses* (IPRV) were prepared as described by Perrin, P., 1996, supra. Virus was purified from inactivated (β-propiolactone) and clarified infected-cell supernatants by ultracentrifugation through a sucrose gradient. PV glycoprotein was solubilized from IPRV and purified (G PV) as previously described by Perrin, P., 1996, supra and Perrin, P., et al., 1985, "Rabies immunosomes (subunit vaccine) structure and immunogenicity", *Vaccine*, 3:325–332.

The two inactivated rabies virus used for comparative protection studies were prepared with two different strains: 1) PM as commercial vaccine for human use; (Pasteur Vaccins Marnes-la-Coquette France; Lot Y0047); 2) PV as a vaccine for laboratory use (IPRV).

Construction of plasmids expressing *lyssavirus* G genes. The region (amino acids 253–275) overlapping the only non-conformational epitope (VI) (FIG. 1) was chosen for the construction of chimeric genes because it is presumably less structurally constrained than the two major antigenic sites II and III. The homogeneous and chimeric *lyssavirus* G genes (see FIG. 1) were introduced into the eukaryotic expression vector pClneo (Promega), propagated and amplified in *E. coli* strain DH5α by standard molecular cloning protocols well known to the skilled artisan. Plasmids pGPV-PV and pGMok-PV were prepared as previously described (Bahloul, C., et al., 1998, "DNA-based immunization for exploring the enlargement of immunological cross-reactivity against the *lyssaviruses*", *Vaccine* 16:417–425). Plasmids pGPV-Mok, pG-PVIII and pGEBL1-PV were obtained as follows.

For pGPV-Mok, the coding sequence of the site II part of G PV (amino acids 1–257) was amplified by RT-PCR using degenerated primers:
PVXbaI: (SEQ ID NO.:1)
PVBclI: (SEQ ID NO.:2)

The PCR product was inserted into the SmaI site of pUC19, then excised with BclI and EcoRI and ligated between the same sites in pGMok-Mok giving pGPV-Mok, containing an in-frame fusion of amino acids 1–257 from G PV with amino acids 258–503 from G Mok.

The pG-PVIII gene, with an internal in-frame deletion between the end of the PV signal peptide and residue 253, was obtained by introducing a synthetic adaptor between the EcoRI and BclI restriction sites of the pGMok-PV plasmid. This PV adaptor, containing a single EcoRI site, was generated by annealing 200 picomoles of each primer in 250 mM Tris-HCl pH 7.7. pGPVIII was deposited on Dec. 22, 1998 with the Collection Nationale de Cultures de Microorganismes (CNCM), Paris, France, and given Accession Number I-2115.
PVp1: (SEQ ID NO.: 3)
Pvp2: (SEQ ID NO.:4)

To generate the pGEBL1-PV gene, a synthetic adaptor corresponding to amino acids 2–14 from EBL-1a (strain 8615POL) (1) single BstEII and EcoRI restriction sites were generated in the same way as that for pG-PVIII, by annealing:
EBL1p1: (SEQ ID NO.:5)
EBL1p2: (SEQ ID NO.:6)

This EBL1 adaptor was ligated in-frame into the EcoRI site of pG-PVIII. A fragment corresponding to amino acids 15–253 from EBL-1a (strain 8615POL) was then generated by RT-PCR of viral RNA using primers EBL1p3 and EBL1p4:
EBL1p3: (SEQ ID NO.:7)
EBL1p4: (SEQ ID NO.:8)

The RT/PCR product was digested with BstEII and EcoRI and was ligated into the same sites introduced via the EBL1 adaptor, resulting in an in-frame fusion between the PV signal peptide, the EBL1a site II part and the PV site III part. The identity of each construct was confirmed by automatic sequencing with dye terminator reaction on an ABI 377 sequencer (Perkin-Elmer). pEBL1-PV was deposited with the CNCM on Dec. 22, 1998, and assigned the Accession Number I-2114.

Insertion of foreign B and CD8 cell epitopes in truncated or chimeric G genes. The previously reported truncated (pGPVIII) and chimeric genes (pGEBL1-PV) containing a unique EcoRI cloning site were used for the insertion of foreign B and CD8 cell epitopes. Lyssavirus G genes were introduced into the eukaryotic expression vector pCIneo (Promega), propagated and amplified in Escherichia coli strain DH5α by standard molecular cloning protocols.

B and CD8 cell epitopes were inserted into the EcoRI restriction site of the truncated or chimeric lyssavirus G genes in the hinge region (amino acids 253 to 275) of the molecule at position 253. The B cell epitope (named *B+) corresponded to fragment C3 (amino acid 93 to 103: DNPASTTNKDK: SEQ ID NO.:9) of the poliovirus VP1 protein. The CD8 cell epitope (named *CTL+) corresponded to amino acids 119–127 (PQASGVYMG: SEQ ID NO.:10) or amino acids 117–132 (ERPQASGVYMGNLTAQ: SEQ ID NO.:11) of the lymphocyte choriomeningitis virus nucleoprotein. Plasmids p(B-CTL)2-GPVIII, pGEBL1-(B)-PV, pGEBL1-(CTL)-PV, pGEBL1-(B-CTL)-PV, pGEBL1-(B-CTL)₂-PV, and pGEBL1-(CTL-B)-PV were obtained as follows (see also FIG. 1):

The p(B-CTL)2-GPVIII gene was generated by a two step cloning of a synthetic adapter in the unique EcoRI restriction site by annealing 200 picomoles of each primer:
*B-CTLp1+: (SEQ ID NO.:12)
*B-CTLp2+: (SEQ ID NO.:13).

For pGEBL1-(B)-PV, pGEBL1-(CTL)-PV, the synthetic adaptors used for the insertion were respectively:
B: *Bp3+: (SEQ ID NO.:14)
*Bp4+: (SEQ ID NO.:15)
CTL: *CTLp5+: (SEQ ID NO.: 16)
*CTLp6+: (SEQ ID NO.:17).

For pGEBL1-(B-CTL)-PV and pGEBL1-(CTL-B)-PV plasmid construction, pGEBL1-(B)-PV and pGEBL1-(CTL)-PV were used under the same conditions as above to insert CTL and B sequences, respectively, in the chimeric genes.

The identity of each construct was confirmed by automatic sequencing with dye terminator reaction on an ABI 377 sequencer (Perkin-Elmer).

Transient expression experiments. The ability of plasmids to induce transient expression of G related antigens was tested after transfection of Neuro 2a cells using the DOTAP cationic liposome-mediated method according to the manufacturers instructions (Boehringer Mannheim). Each well of a cell culture microplate (Falcon) was inoculated with $3 \times 10^4$ cells (in MEM, 10% FBS) and incubated for 24 h at 37° C. in a humidified atmosphere containing 7.5% $CO_2$. The plate was then washed with MEM without FBS and incubated as above for 1 h. The cell supernatant was removed, and the wells were washed and filled with a total volume of 50 μl transfection solution, which contained 0.1 μg plasmid and 6 μl DOTAP ((N-(1–2,3,-dioleoyloxy)propyl)-N,N,N-trimethylammoniummethyl-sulfate) in sterile HEPES-buffered saline (150 mM NaCl, 20 mM HEPES) previously incubated at room temperature for 15 min. The plates were incubated for 5 h at 37° C. in the presence of 7.5% $CO_2$. Two hundred μl MEM containing 2% FBS were added to each well and the plate was incubated for 24 to 140 h in the same conditions, before analysis of transient expression by indirect immunofluorescence.

The ability of plasmids to induce transient expression of G and foreign related antigens was tested after transfection of Neuro 2a cells using the FuGENE 6 transfection reagent according to the manufacturer's instructions (Boehringer Mannheim). Each well of a cell culture Labtek chamber Nunc (Life Technologies) was inoculated with $3 \times 10^4$ cells (in MEM, 10% FBS) and incubated for 24 h at 37° C. in a humidified atmosphere containing 7.5% $CO_2$. The plates were then washed with MEM without FBS and wells were filled with 50 μl transfection solution: 0.1 μg plasmid, 3 μl of FuGENE 6 transfection reagent, and 47 μl of Medium. The plate was incubated for 18 h at 37° C. in the presence of 7.5% $CO_2$. Two hundred μl MEM containing 5% FBS were added to each well and the plate was incubated another 24 h under the same conditions before analysis of transient expression by indirect immunofluorescence.

Antibodies. Polyclonal antibodies (PAb) directed against PV and Mok G were obtained as described by Perrin, P., 1996, "Techniques for the preparation of rabies conjugates", In *Laboratory techniques in rabies*, Meslin, F-X., Kaplan, M., and Koprowski, H. Eds. (WHO Geneva).:433–445, by rabbit immunization with purified virus glycoprotein. PAb against EBL-1b virus was obtained by mouse immunization with inactivated and purified virus.

Three monoclonal antibodies (MAb) directed against PV G were also used. PVE12 MAb (a MAb developed by M. Lafon et al., 1985, "Use of a monoclonal antibody for quantitation of rabies vaccine glycoprotein by enzyme immunoassay", *J. Biol. Standard* 13:295–301) recognizes site II of native G. D1 MAb (IgG 1 isotype), produced in our laboratory, recognizes site III of native but not SDS-treated G. 6A1 MAb (a MAb reported in 18 of 2) recognizes SDS-denatured G protein and more precisely two peptides located downstream from site III, near the COOH-terminal part of the G ectodomain (amino acids 342–433 and 397–450).

Immunofluorescence microscopy. Transient expression of G antigens in transfected cells was assessed with and without permeabilization (30 min incubation with 80% acetone on ice followed by air drying). Transfected cells were incubated for 1 h at 37° C. with PAb or MAb. They were washed with PBS, and incubated for 1 h at 37° C. with goat anti-rabbit or anti-mouse FITC-conjugated secondary antibody (Nordic Immunol. Labs, The Netherlands). Cells were washed, mounted in glycerol, and examined in a Leica inverted fluorescence microscope.

Two mouse monoclonal antibodies directed against PV G (D1 MAb IgG 1 isotype) and poliovirus (C3 MAb) were used for antigen staining by indirect immunofluorescence (IIF). D1 MAb recognizes the site III of native but not SDS-treated G and C3 Mab recognizes the 93–103 region of the PV-1 capsid VP1 protein. A rabbit neutralizing polyclonal antibody directed against the native poliovirus type 1 was also used.

Transient expression was assessed after 3% paraformaldehyde (Sigma) fixation (20 min incubation at room temperature) without permeabilization. Fixed cells were incubated for 1 h at room temperature with MAb. They were washed with phosphate-buffered saline (PBS), and incubated for 1 h at room temperature with goat anti-mouse or anti-rabbit FITC-conjugated secondary antibody (Nordic Immunol. Labs, The Netherlands). Cells were washed, mounted in Mowiol (Sigma) and examined in a Leica inverted fluorescence microscope.

Putative PEST sequence analysis. Polypeptide PEST sequences potentially involved in rapid degradation of protein were analyzed with the computer program PEST find developed according to Rogers, S. et al., 1986, "Amino acid sequences common to rapidly degraded proteins: the PEST hypothesis", *Science* 234:364–369.

Injection of plasmids into mice. For immunological studies, BALB/c mice were anesthetized with pentobarbital (30 mg/kg) and 20–50 µg plasmid (diluted in PBS) was injected into each anterior tibialis muscle. This was more effective than injection via the quadriceps route (personal observation). Blood was collected for antibody assay of serum on various days by retro-orbital puncture.

For protection studies against LCMV, mice received 3.5 µg of cardiotoxin (Latoxan A.P., Les Ulis, France) in each leg four days before anaesthesia and immunization to degenerate the muscle.

Interleukin-2 release assay. Fourteen days after injection, spleens were removed from naive, or plasmid-injected BALB/c mice. Splenocytes (1 ml aliquots containing $6 \times 10^6$) were stimulated with 0.5 µg *lyssavirus* antigen (e.g., IPLV-PV and IPLV-EBL1) or 5 µg concanavilin A (Miles) in 24-well plates (Nuclon-Delta, Nunc) and cultured according to standard procedures in RPMI-1640 medium (Gibco) containing 10% FBS, 1 mM sodium pyruvate, 1 mM non-essential amino acids, $5 \times 10^{-5}$ M 2-mercaptoethanol, 10 mM HEPES buffer (Flow Laboratories). Cells were incubated for 24 h at 37° C. in a humidified atmosphere containing 7% $CO_2$. Under these conditions, cells producing IL-2 are mainly $CD4^+$ cells. IL-2 produced in supernatants of splenocyte cultures was titrated by bioassay using CTLL cells as previously described by Perrin, P. et al., 1996, "The antigen-specific cell-mediated immune response in mice is suppressed by infection with pathogenic *lyssaviruses*", *Res. Virol.* 147:289–299. Cell proliferation was determined in triplicate, based on the uptake of $^3$H-thymidine (New England Nuclear). IL-2 concentration was determined as units per ml (U/ml) using mouse recombinant IL-2 (Genzyme Corporation, Cambridge, Mass., USA) as the reference. CTLL cells grew in the presence of mouse IL-2 and anti-IL-4 antibodies but not in the presence of IL-4 (up to 10 U/ml) and in the absence of IL-2. So, IL-2 was predominantly detected by this technique.

Antibody assays. For antibody assay of serum, blood was collected on various days by retro-orbital puncture. Rabies IgG were titrated by enzymze-linked immunosorbent assay (ELISA) using microplates coated with purified rabies glycoprotein. Titer corresponded to the reciprocal dilution of the serum sample giving the optical density equivalent to twice that given by serum (diluted 1/20) of PBS injected mice. Total antirabies IgG or IgG1, IgG2a and IgG3 isotypes were assayed by ELISA using microplates coated with IPRV as previously described by Perrin, P. et al., 1986, "The influence of the type of immunosorbent on rabies antibody EIA; advantages of purified glycoprotein over whole virus", *J. Biol. Standard.* 14:95, with rabbit anti-mouse IgG isotype sera as the secondary antibody (Nordic Immunol. Labs, The Netherlands) and a goat anti-rabbit IgG peroxidase conjugate (Nordic Immunol. Labs, The Netherlands) as the tertiary antibody.

*Lyssavirus* neutralizing antibodies were titrated by the rapid fluorescent focus inhibition test (RFFIT) (described by Smith, J. et al., 1996, "A rapid fluorescent focus inhibition test (RFFIT) for determining virus-neutralizing antibody", In *Laboratory techniques in rabies*, Fourth edition (Eds Meslin, F-X; Kaplan, M and Koprowski, H) WHO, Geneva.: 181–189) with the previously described modifications of Perrin, P. et al., 1986, *J. Biol. Standard.* 14:95. Infected cell supernatants (PV, CVS, and EBL2 viruses) and purified viruses (Mok and EBL1 viruses) were used. Anti-PV or CVS antibody titers are expressed in international units per ml (IU/ml) using the 2nd International Standard (Statens Seruminstitut, Copenhagen, Denmark) as the reference. For antibody titer determination against other *lyssaviruses*, the serum dilution causing 50% inhibition of the fluorescent focus rate was defined as having the same VNAb titer as for reference assayed against CVS.

Antibodies to PV-1 were assayed by ELISA as previously described using microplates coated with a synthetic peptide constituted by a trimer of amino acids 93–103 of VP1. Anti-LCM IgG production was also tested by ELISA.

Protection test. The protective activity of vaccines and plasmids was determined according to the NIH potency test. Dilutions of vaccine were injected intra-peritoneally (i.p.) into mice on days 0 and 7 whereas plasmids (40 µg) were injected into each anterior tibialis muscle on day 0 only. Mice were then intra-cerebrally (i.c.) challenged on day 21 with about 30 $LD_{50}$ of various *lyssaviruses* (CVS, LCMV, EBL1b, or EBL2b). Animals were observed for 28 days or alternatively sacrificed at day 21 post-challenge and blood samples collected in order to control the virus clearance and the anti-LCMV IgG production.

Example 1

Transient Expression of *Lyssavirus* G Genes

Plasmids containing homogeneous (pGPV-PV), truncated (pG-PVIII), and chimeric (pGEBL1-PV, pGMok-PV and pGPV-Mok) *lyssavirus* G genes were used to transfect Neuro 2a cells. Cell staining by indirect immunofluorescence is reported in FIG. 2 and can be summarized as follows.

After transfection with pGPV-PV, antigen was detected with PV PAb (FIG. 2A), PV D1 MAb (FIG. 2B), or PV E12 Mab (not shown), mostly at the cell membrane (similar results with non-permeabilized cells, data not shown) and very few detected with 6A1 Mab (FIG. 2C). Cells transfected with pG-PVIII were round in shape and completely stained (both cytoplasm and membrane) with PV PAb (FIG. 2D) or 6A1 MAb (FIG. 2F), but not with PV D1 MAb (FIG. 2E). Cells transfected with pGEBL1-PV were stained mostly at the cell membrane with PV PAb (FIG. 2G), PV D1 MAb (FIG. 2H), or EBL-1 PAb (FIG. 2I). Cells transfected with pGMok-PV were stained (mainly at the membrane) with PV PAb (FIG. 2J), PV D1 MAb (FIG. 2K), Mok PAb (FIG. 2L), and very few stained with 6A1 MAb (not shown). Cells transfected with pGPV-Mok were stained with PV PAb (FIG. 2M) or Mok PAb and round in shape (FIG. 2N). Cell transfection distinguishes two types of G antigens: 1) stained principally at the membrane of cells normal in shape, in particular using neutralizing Mab directed to site II (PV E12) and III (PV D1); and 2) stained in both the cytoplasm and membrane of cells round in shape, in particular using MAb (6A1), which recognizes the denatured G molecule.

The kinetics of G protein expression was studied upon transfection of cells with three representative plasmids: pGPV-PV (homogenous), pGEBL1-PV (chimeric), and pG-PVIII (truncated). pGPV-PV produced G antigens in about 60% of cells when stained with PV PAb, whereas very few cells were stained with PV 6A1 MAb at any time point (FIG. 3a). About 55% of cells transfected with pGEBL1-PV were stained with PV PAb and up to 15% with 6A1 MAb (FIG. 3b) indicating that some G molecules were denatured. Ten to twenty percent of cells transfected with pG-PVIII were round in shape and stained with PV PAb whereas 5 to 10% were positive with 6A1 MAb, indicating that G molecules were denatured (FIG. 3c).

Example 2

Induction of IL-2-Producing Cells

The ability of the plasmids, pGPV-PV, pG-PVIII, pGEBL1-PV, pGMok-PV and pGPV-Mok to induce IL-2-producing cells was assayed and the results are shown in FIG. 4. Plasmids with the site III part of PV, whether unfused (pG-PVIII) or with any *lyssavirus* site II part (pGPV-PV, pGEBL1-PV and pGMok-PV), efficiently induced IL-2 producing cells (240 to 550 mU/ml). This was true even for pG-PVIII, which, however, had only low efficiency for both cell transfection (see above) and antibody induction (see below). For the chimeric plasmids EBL1-PV and Mok-PV, the T-cell response was greater after stimulation with inactivated and purified PV than with EBL-1b or Mok viruses. This was not due to the quality of the purified antigens because immunization of BALB/c mice with PV, EBL-1b, or Mok inactivated and purified virus followed by in vitro stimulation with the same antigen induced similar levels of IL-2 production (PV: 250 mU/ml, EBL-1b: 350 mU/ml and Mok: 400 mU/ml). In contrast, the plasmid pGPV-Mok induced only a weak Th cell response (IL-2 titer: 50 mU/ml), which was similarly produced in vitro after stimulation with either inactivated and purified PV or Mok virus.

Example 3

Serological Assays

The truncated pG-PVIII plasmid did not induce the production of rabies antibodies, when assayed by RFFIT and ELISA. However when IL-2 was injected together with pG-PVIII, and then alone 7 days later, antibodies were detected on day 21 only by ELISA (data not shown). Thus, the site III part was expressed in vivo and induced a weak production of non-neutralizing antibodies, which was boosted by exogenous IL-2.

In contrast, when the site III part of PV was linked with the homologous site II part, as in pGPV-PV, it displayed strong immunogenicity. A single injection of pGPV-PV plasmid into mice resulted in high levels of VNAb measured 27 days later against both the homologous PV and CVS viruses and the heterologous EBL-2b virus (FIG. 5a). The antibody isotype induced was mainly IgG 2a, but a weak IgG 1 response was also observed (data not shown). However, the correlation between VNAb titers against PV was stronger with IgG 2a ($r=0.974$) than with IgG 1 titer ($r=0.71$), indicating that VNAb induced by DNA-based immunization were mainly IgG 2a. The VNAb titer against the homologous PV and CVS viruses increased when mice received a booster injection on day 30 and their sera were checked at day 40, but not the VNAb titers against the heterologous EBL-2b virus which remained unchanged (FIG. 5a). In these conditions we also demonstrated a relationship between VNAb level induced by pGPV-PV and the protection of mice against an i.c. challenge with CVS: all animals with a VNAb titer (on day 20) above 1.5 IU/ml survived the challenge on day 21 (not shown). In contrast, no significant amount of VNAb against EBL-1b was produced after a single injection or after a boost.

Thus, we investigated the capability of the site III part of PV to carry the heterologous EBL1 site II part, following our previous observation that the chimeric plasmid pGMok-PV induced VNAb against both PV and Mok viruses. A single injection of the chimeric plasmid pGEBL1-PV similarly induced VNAb against both PV and EBL-1b viruses (FIG. 5b). Fourteen days after injection, titers were 2 IU/ml and they increased to 17 IU/ml after 80 days. The level of VNAb production against EBL-1b was always higher than that against PV, but the difference was not significant.

Taken together, these results clearly demonstrate that chimeric G genes encoding the site III part of PV and the site II part of G of other *lyssaviruses* such as EBL-1b or Mok are very potent inducers of VNAb against both parental viruses. In contrast, the symmetric pGPV-Mok construct did not induce VNAb against either PV or Mok viruses (not shown).

Example 4

Protection Assays Against European *Lyssaviruses*

We tested the ability of both the homogenous pGPV-PV and the chimeric pGEBL1-PV plasmid to induce protection against an i.c. challenge with viruses representing *lyssavirus* genotypes involved in the transmission of encephalomyelitis in Europe (CVS for GT1, EBL1b for GT5, and EBL2b for GT6). We compared their efficiency with that of a commercially available vaccine (PM strain: GT1) and a laboratory preparation (PV strain: GT1) (FIG. 6).

The plasmid backbone (pClneo) did not induce protection against any virus (FIGS. 6d, e, and f). In contrast, pGPV-PV protected 70% of BALB/c (and 85% of swiss) mice against CVS (FIG. 6d), 30% against EBL1b (FIG. 6e), and 72% against EBL2b (FIG. 6f). In the same conditions, pGEBL1-PV protected 60% of BALB/c mice against CVS (FIG. 6d), 75% against EBL1b (FIG. 6e) and 80% against EBL2b (FIG. 6f). Thus, if immunization with any of the two plasmids showed no significant difference in the protection against CVS (GT1) and EBL2b (GT6), the chimeric pGEBL1-PV was far more efficient against EBL1b (GT5) and is clearly the best candidate for protection with DNA-based immunization against the three European *lyssavirus* genotypes.

Concerning the protection induced by inactivated cell culture vaccines using the PM and PV strains against the same challenges: a human dose of PM vaccine diluted 1/10th protected 80% of mice against CVS (FIG. 6a), 36% against EBL1b (FIG. 6b), and 80% against EBL2b (FIG. 6c). Under the same conditions, 2 µg of PV IPRV protected 100% of mice against both CVS (FIG. 6a) and EBL1b (FIG. 6b) and 85% against EBL2b (FIG. 6c). It seems that for a vaccine dose that protected 80 to 85% of the animals against EBL2b, the PV strain protected 100% and PM strain only 36% against EBL1b. Thus, the PM strain is less effective than the PV strain against EBL1b.

Example 5

Transient Expression of *Lyssavirus* G Genes

Plasmids containing the foreign antigen encoding sequences associated with the truncated (pG-PVIII) or chimeric (pGEBL1-PV) *lyssavirus* G genes were tested for their ability to transiently transfect Neuro 2a cells. Except for pG(B-CTL)$_2$-PVIII, which induced an IIF staining (in the cytoplasm) only after permeabilization, all plasmids induced the expression of polio- and *lyssaviruses* related antigens at the cell membrane of non-permeabilized cells as previously reported for the same plasmids without foreign epitopes.

For illustration, transfection results obtained with pGEBL1-(B-CTL)$_2$-PV are reported in FIG. 7. Both rabies virus G part recognized by PV D1 MAb (FIG. 7A) and poliovirus insert recognized either by the C3 MAb (FIG. 7B) or the anti poliovirus type 1 PAb (FIG. 7C) were evidenced, whereas no staining was observed with the same MAb and PAb on PClneo transfected cells (FIG. 7D). This clearly indicates that, except for pG(B-CTL)$_2$-PVIII, the chimeric pGEBL1-PV glycoprotein allowed the expression of the poliovirus B cell epitope alone or in association with the LCMV CTL cell epitope at the cell surface membrane under a native form whereas the expression of *lyssavirus* G was maintained.

Example 6

Immunogenicity of Foreign Epitopes Carried by the Truncated Glycoprotein

The truncated pGPVIII gene was used to carry and expressed C3 VP1 B cell and LCMV CD8$^+$ CTL epitopes in mice after DNA-based immunization.

While the pGPVIII gene induced IL-2 producing cells that can be in vitro stimulated by IPRV 21 days after injection, no production was observed after 14 days (FIG. 8A). However, a significant production was observed with pG(B-CTL)$_2$-GPVIII after 14 days (FIG. 8A). This indicates that the fusion of foreign epitopes with GPVIII significantly enhances the production of Th cells directed to site III part of rabies G.

Although pGPVIII induced no antirabies antibody in the absence of exogenous IL-2 (FIG. 9), the kinetic study of antibody induced by pG(B-CTL)$_2$-GPVIII showed that significant antibody production occurred against both rabies G and poliovirus peptide (FIG. 9) This also indicates that the fusion of foreign epitopes with GPVIII significantly enhances the production of antibody directed to site III part of rabies PV G. Moreover, the truncated GPVIII was able to carry and to allow the expression of poliovirus B cell epitope in vivo with antibody production.

Production of antibodies induced by p(B-CTL)$_2$-GPVIII against a poliovirus peptide was also tested after priming with either pGPVIII or p(B-CTL)$_2$-GPVIII itself (FIG. 10). When p(B-CTL)$_2$-GPVIII was injected without priming and controlled 13 days (PBS/p(B-CTL)$_2$-GPVIII-D26-) or 39 days after (p(B-CTL)2-GPVIII-D0-), antipeptide antibody titer was 65 and 80, respectively. However, if a priming was performed with pGPVIII or p(B-CTL)$_2$-GPVIII, the titer was 200 and 600, respectively. This clearly demonstrates that the two types of priming enhanced antibody production against a poliovirus peptide.

Example 7

Immunogenicity of Foreign Epitopes Carried by the Chimeric Glycoprotein

Immunogenicity of both B and CD8 T cell epitopes and the consequence of their insertion on the immunogenicity of the chimeric glycoprotein were analyzed according to humoral and cell mediated immune responses after DNA-based immunization. When epitopes were inserted in the chimeric pGEBL1-PV plasmid, the induction of IL-2-producing cells able to be stimulated by IPLV depended on inserted epitopes. Two types of results were obtained, and are shown in FIG. 8B: i) IL-2 production induced by pGEBL1-(B-CTL)$_2$-PV, pGEBL1-(CTL-B)-PV, and pGEBL1-(CTL)-PV was similar to that induced by pGEBL1-PV; and ii) IL-2 production induced by pGEBL1-(B-CTL)-PV (data not shown) and pGEBL1-(B)-PV was inhibited. Consequently, it seems that the chimeric G EBL1-PV can carry foreign B and CD8 T cell epitopes without negative effects on its ability to induce IL-2-producing cells. However, concerning the B cell epitope, a position effect was observed since its insertion immediately behind the EBL1 sequence was deleterious for the induction of T helper cells stimulated by *lyssavirus* G. However, this phenomenon was not evidenced with pGEBL1-(B-CTL)$_2$-PV.

Insertion of foreign epitopes in pGEBL1-PV was also studied for its consequence on the induction of antibodies against poliovirus peptide and VNAb against both PV and EBL1 *lyssaviruses* (Table 1). The four plasmids containing the B cell epitope (pGEBL1-(B)-PV, pGEBL1-(CTL-B)-PV, pGEBL1-(B-CTL)$_2$-PV, and pGEBL1-(B-CTL)-PV) induced antibody against the poliovirus peptide. However, when the B cell epitope followed EBL1 sequence (pGEBL1-(B-CTL)-PV and pGEBL1-(B)-PV), antibody production was weaker than when the B epitope was separated by the CD8 cell epitope (pGEBL1-(CTL-B)-PV). The results for pGEBL1-(B-CTL)$_2$-PV were intermediary. The insertion of foreign epitopes induced a decrease of anti-*lyssavirus* VNAb production but was maintained at a high level when animals were injected with pGEBL1-(CTL)-PV or pGEBL1-(CTL-B)-PV. However, when the B cell epitope was inserted immediately behind the EBL1 sequence, not as great of an anti-*lyssavirus* VNAb production was observed.

In summary, the chimeric G EBL1-PV can carry and allow the in vivo expression of both poliovirus and *lyssavirus* neutralizing B cell epitopes but, the presence of the poliovirus B cell epitope immediately behind the EBL1 sequence (excepted for (B-CTL)$_2$ insertion) is deleterious for the immunogenicity of both the site II and site III part of the chimeric glycoprotein. On the other hand, when the foreign epitopes were fused with the truncated G PVIII, both T helper and non-neutralizing antibody production can be induced.

Example 8

Protection Against a Lethal Dose of LCMV

As the CD8 T cell epitope is involved in the induction of protection against LCMV, the truncated and chimeric G carrying the LCMV CD8$^+$ T cell epitope were tested for their protective activity (Table 2). The truncated p(B-CTL)$_2$-GPVIII induced only a partial protection. When the B and CD8 T cell epitopes were inserted into the chimeric GEBL1-PV a significant protection was observed with pGEBL1-(CTL-B)-PV against a lethal challenge with LCMV (70% of mice survived). Under these conditions, the surviving animals completely eliminate the virus when controlled by RT-PCR 21 days post-infection (data not shown). This indicates that the chimeric G is very potent to carry a protective CD8 cell epitope. However, as for anti-*lyssavirus* and poliovirus immune responses, the insertion of the poliovirus B cell epitope immediately behind the EBL1 sequence induced an inhibition of the protective activity of the following CD8 cell epitope.

Example 9

Putative PEST Sequence

Since a deleterious position effect was clearly observed for the position of the insertion of the B cell epitope before or after the CTL cell epitope, the presence of putative PEST sequences in the different plasmids was analyzed (FIG. 1*d*). Only two plasmids (pGEBL1-(B)-PV and pGEBL1-(B-CTL)$_2$-PV) contained putative PEST sequences due to the junction of the end of EBL1 and the B cell epitope sequences. However, the substitution of the serine (S) in pGEBL1-(B-CTL)$_2$-PV by a leucine (L) in pGEBL1-(B)-PV reduced the PEST value from +8.38 to +4.20.

Example 10

Dog Immunization and Challenge

Beagle dogs ranging in age from 4 to 8 years were assigned in four experimental groups (Table 3). They were kept in isolated cages and fed with commercial food (400 g each day). They were injected intramusculary in the thigh with either with 100 µg of plasmid (group A, B and C) or PBS (group D). Plasmid was injected in one site on day 0, 21, 42, and 175 (group A) or on day 0 and 175 (group C). It was also injected in three sites (3×33 µg) on day 0, 21, 42, and 175 (group B). Blood samples were collected (from veinpuncture) on day 0, 28, 49, 70, 120, 175, and 189.

*Lyssavirus* neutralizing antibodies were titrated by the rapid fluorescent focus inhibition test (RFFIT) with the previously described modifications of (28 of the dogs) using PV, CVS or FWR viruses) cell. Anti-PV, CVS, or FWR neutralizing antibody titers are expressed in international units per ml (IU/ml) using the 2nd International Standard (Statens Seruminstitut, Copenhagen, Denmark) as the reference or as the reciprocal serum dilution that inhibit 50% of fluorescent focus. Under these conditions, a titer of 40, 70, or 60 (reciprocal serum dilution) was equivalent to 0.5 IU/ml against PV, CVS or FWR respectively.

As shown in FIG. 11, a virus neutralizing antibody (VNAb) can be induced by the plasmid containing the gene encoding the G protein groups (A, B, and D), whereas no antibody was detected in PBS injected animals (group D) whatever the injection protocol. Heightened levels of VNAb were obtained after one injection and a boost on day 21 (group A) or on day 175 (group C). As the seroconversion occurs for 0.5 IU/ml, it can be concluded that all animals have serconverted. Moreover, according the literature it can also be concluded that all plasmid-injected dogs are protected against a rabies virus challenge.

These results are representative and the dosage can be extrapolated to other rabies susceptible animals, including humans.

Example 11 pG-PVIII as a Carrier for Foreign Protein: *P. falciparum* Domain Mediating Adhesion to Chondroitin Sulfate A: a Receptor for Human Placental Infection Malaria during the first pregnancy causes a high rate of fetal and neonatal death. The decreasing susceptibility during subsequent pregnancies correlates with acquisition of antibodies that block binding of infected red cells to chondroitin sulfate A (CSA), a receptor for parasites in the placenta. Recently, the inventors identified a domain within a particular *Plasmodium falciparum* erythrocyte membrane protein-1 (PfEMP-1) that binds CSA (Buffet et al. *P. falciparum* domain mediating adhesion to chondroitin sulfate A: A receptor for human placental infection (1999) *P.N.A.S.* 96:12743–12748). The inventors cloned a var gene expressed in CSA-binding parasitized red blood cells (PRBCs). The gene had eight receptor-like domains, and the inventors demonstrated that the Duffy-binding-like (DBL) domain called DBL-3 bound CSA and displays the same binding specificity as PRBCs.

As protective antibodies present after pregnancy block binding to CSA of parasites from different parts of the world, DBL-3, although variant, may induce cross-reactive immunity that will protect pregnant women and their fetuses. Thus, the DBL-3 domain becomes a candidate as a vaccine for pregnant women in Africa.

The DBL-3 domain contains a number of cysteines, which seem to be crucial for the correct folding of the CSA binding region. This folding can most likely, not be achieved in bacterial expression systems (unpublished data). One important approach to induce antibodies capable to interfere with the CSA binding of infected erythrocytes is to apply a DNA vaccine strategy using the DBL-3 domain fused to the rabies PV III part. The rabies glycoprotein PVIII part has been shown to promote efficient helper function.

The invention has been described in detail above with reference to preferred embodiments. However, it will be understood by the ordinary artisan that various modifications and variations can be made in the practice of the present invention without departing from the scope or spirit of the invention. All references cited herein are hereby incorporated by reference in their entirety.

TABLE 1 shows the protection induced by the chimeric pGEBL1-PV plasmid carrying the LCMV CD8+ epitopes. BALB/c mice (three for each plasmid) were injected with 40 μg of various plasmids and i.c. challenged on day 21. Percentage of surviving animals is reported in brackets.

TABLE 1

Antibody production induced by the chimeric pGEBL1-PV plasmid carrying various combinations of B and CD8+ T cell foreign epitopes

| Plasmid injected | Neutralizing antibody (IU/ml) against: | | Poliovirus anti-peptide antibody (Reciprocal dilution) |
|---|---|---|---|
| | Rabies virus | European Bat Lyssavirus 1 | |
| pGEBL1-(B-CTL)2-PV | 0.9 (0.05) | 1.1 (0.07) | 1100 (200) |
| pGEBL1-(CTL-B)-PV | 1.8 (0.2) | 8.0 (1.0) | 1510 (490) |
| pGEBL1-(B-CTL)-PV | 0.06 (0.06) | 0.6 (0.07) | 810 (210) |
| pGEBL1-(CTL)-PV | 2.6 (0.2) | 5.2 (0.2) | 0 (0) |
| pGEBL1-(B)-PV | 0.1 (0.01) | 0.21 (0.09) | 355 (45) |
| pGEBL1-PV | 5.9 (2.1) | 21.9 (1.8) | 0 (0) |
| pCIneo | 0 (0) | 0 (0) | 0 (0) |

TABLE 1 shows antibody production induced by the chimeric pGEBL1-PV plasmid carrying various foreign epitopes. BALB/c mice (three for each plasmid) were injected with 50 μg of various plasmids in each tibialis muscle. Sera were assayed on day 21 for rabies or EBL1 virus neutralizing antibody by the RFFIT method (titer expressed in IU/ml) and for poliovirus anti-peptide antibody by ELISA. Results are expressed as the mean titer, and standard deviation are reported in brackets.

TABLE 2

Protection induced by the truncated pGPVIII and the chimeric pGEBL1-PV plasmid encoding the LCMV CD8+ epitope

| Plasmid injected | Survival animals (%) |
|---|---|
| pCIneo | 0/10 (0) |
| p(B-CTL)2-GPVIII | 2/5 (40) |
| pGEBL1-(B-CTL)-PV | 0/10 (0) |
| pGEBL1-(CTL-B)-PV | 7/10 (70) |

TABLE 3

Dog characteristics and injection protocol

| Group | Dog number | Sex* | Age (years) | Product injection | Site Number | Day |
|---|---|---|---|---|---|---|
| A | 1 | M | 8 | Plasmid | 1 | 0, 21, 42 and 175 |
| | 2 | F | 6 | Plasmid | 1 | 0, 21, 42 and 175 |
| | 3 | F | 6 | Plasmid | 1 | 0, 21, 42 and 175 |
| B | 4 | F | 6 | Plasmid | 3 | 0, 21, 42 and 175 |
| | 5 | M | 6 | Plasmid | 3 | 0, 21, 42 and 175 |
| | 6 | F | 8 | Plasmid | 3 | 0, 21, 42 and 175 |
| C | 7 | M | 4 | Plasmid | 1 | 0 and 175 |
| | 8 | F | 7 | Plasmid | 1 | 0 and 175 |
| | 9 | F | 4 | Plasmid | 1 | 0 and 175 |
| D | 10** | M | 4 | PBS | 1 | 0, 21, 42 and 175 |
| | 11 | M | 4 | PBS | 1 | 0, 21, 42 and 175 |
| | 12 | M | 4 | PBS | 1 | 0, 21, 42 and 175 |

*M: male; F: female
**Discarded on day 160 (sick)

SEQUENCE LISTING

<160> NUMBER OF SEQ ID NOS: 17

<210> SEQ ID NO 1
<211> LENGTH: 34
<212> TYPE: DNA
<213> ORGANISM: Rabies virus

<400> SEQUENCE: 1
ttctagagcc accatggttc ctcaggctct cctg       34

<210> SEQ ID NO 2
<211> LENGTH: 23
<212> TYPE: DNA
<213> ORGANISM: Rabies virus

-continued

```
<400> SEQUENCE: 2
attgatcaac tgaccgggag ggc                                           23

<210> SEQ ID NO 3
<211> LENGTH: 98
<212> TYPE: DNA
<213> ORGANISM: Artificial Sequence
<220> FEATURE:
<223> OTHER INFORMATION: Description of Artificial Sequence: synthetic
      adaptor primers

<400> SEQUENCE: 3
aattctagag ccgccaccat ggttcctcag gctctcctgt ttgtacccct tctggttttt    60
ccattgtgtt ttgggaagaa ttccccccccc ggtcagtt                          98

<210> SEQ ID NO 4
<211> LENGTH: 98
<212> TYPE: DNA
<213> ORGANISM: Artificial Sequence
<220> FEATURE:
<223> OTHER INFORMATION: Description of Artificial Sequence: synthetic
      adaptor primers

<400> SEQUENCE: 4
gatcaactga ccgggggggg aattcttccc aaaacacaat ggaaaaacca gaaggggtac    60
aaacaggaga gcctgaggaa ccatggtggc ggctctag                           98

<210> SEQ ID NO 5
<211> LENGTH: 54
<212> TYPE: DNA
<213> ORGANISM: Artificial Sequence
<220> FEATURE:
<223> OTHER INFORMATION: Description of Artificial Sequence: synthetic
      adaptor primers

<400> SEQUENCE: 5
aatttcccaa tctacaccat cccggataaa atcggaccgt ggtcacctat tccg          54

<210> SEQ ID NO 6
<211> LENGTH: 54
<212> TYPE: DNA
<213> ORGANISM: Artificial Sequence
<220> FEATURE:
<223> OTHER INFORMATION: Description of Artificial Sequence: synthetic
      adaptor primers

<400> SEQUENCE: 6
aattcggaat aggtgaccac ggtccgattt tatccgggat ggtgtagatt ggga          54

<210> SEQ ID NO 7
<211> LENGTH: 63
<212> TYPE: DNA
<213> ORGANISM: Rabies virus

<400> SEQUENCE: 7
ccgtggtcac ctattgatat aaaccatctc agctgcccaa acaacttgat cgtggaagat    60
gag                                                                 63

<210> SEQ ID NO 8
<211> LENGTH: 27
<212> TYPE: DNA
<213> ORGANISM: Rabies virus
```

-continued

<400> SEQUENCE: 8
ggaattcgag caccattctg gagcttc                                              27

<210> SEQ ID NO 9
<211> LENGTH: 11
<212> TYPE: PRT
<213> ORGANISM: poliovirus VP1 protein

<400> SEQUENCE: 9

Asp Asn Pro Ala Ser Thr Thr Asn Lys Asp Lys
1 5 10

<210> SEQ ID NO 10
<211> LENGTH: 9
<212> TYPE: PRT
<213> ORGANISM: lymphocyte choriomenigitis virus nucleoprotein

<400> SEQUENCE: 10

Pro Gln Ala Ser Gly Val Tyr Met Gly
1 5

<210> SEQ ID NO 11
<211> LENGTH: 16
<212> TYPE: PRT
<213> ORGANISM: lymphocyte choriomenigitis virus nucleoprotein

<400> SEQUENCE: 11

Glu Arg Pro Gln Ala Ser Gly Val Tyr Met Gly Asn Leu Thr Ala Gln
1 5 10 15

<210> SEQ ID NO 12
<211> LENGTH: 78
<212> TYPE: DNA
<213> ORGANISM: Artificial Sequence
<220> FEATURE:
<223> OTHER INFORMATION: Description of Artificial Sequence: synthetic adaptor primers

<400> SEQUENCE: 12
aattcagata acccggcgtc gaccactaac aaggataagc tgttcgcagt gcctcaggcc 60
tctggtgtgt atatgggt 78

<210> SEQ ID NO 13
<211> LENGTH: 78
<212> TYPE: DNA
<213> ORGANISM: Artificial Sequence
<220> FEATURE:
<223> OTHER INFORMATION: Description of Artificial Sequence : synthetic adaptor primers

<400> SEQUENCE: 13
aattacccat atacacacca gaggcctgag gcactgcgaa cagcttatcc ttgttagtgg 60
tcgacgccgg gttatctg 78

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence : synthetic adaptor primers

<400> SEQUENCE: 14
aatttggata acccggcgtc gaccactaac aa 32

-continued

```
<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence : synthetic
      adaptor primers

<400> SEQUENCE: 15
aattcttatc cttgttagtg gtcgacgccg gg                              32

<210> SEQ ID NO 16
<211> LENGTH: 54
<212> TYPE: DNA
<213> ORGANISM: Artificial Sequence
<220> FEATURE:
<223> OTHER INFORMATION: Description of Artificial Sequence : synthetic
      adaptor primers

<400> SEQUENCE: 16
aatttggaga gacctcaggc ctctggtgtg tatatgggta atcttacggc ccag      54

<210> SEQ ID NO 17
<211> LENGTH: 54
<212> TYPE: DNA
<213> ORGANISM: Artificial Sequence
<220> FEATURE:
<223> OTHER INFORMATION: Description of Artificial Sequence : synthetic
      adaptor primers

<400> SEQUENCE: 17
aattctggga agtaagatta cccatataca caccagaggc ctgaggtctc tcca      54
```

The invention claimed is:

1. A carrier molecule comprising a chimeric polynucleotide sequence, wherein said chimeric polynucleotide sequence comprises a nucleic acid sequence of genotype 1 (GT1) pasteur virus, wherein said nucleic acid sequence of GT1 pasteur virus consists of a sequence encoding amino acids 253–505 of GT1 pasteur virus glycoprotein.

2. The carrier molecule of claim 1, wherein the carrier molecule is a vaccine.

3. The carrier molecule of claim 1, wherein the carrier molecule induces humoral and cellular immunity.

4. An immunogenic composition comprising the carrier molecule of claim 1 and at least one of an adjuvant, excipient, stabilizer, supra molecular vector, or antigen.

* * * * *